US010391498B2

(12) United States Patent
Harder et al.

(10) Patent No.: US 10,391,498 B2
(45) Date of Patent: Aug. 27, 2019

(54) SYSTEMS AND METHODS FOR NUCLEIC ACID AMPLIFICATION

(71) Applicant: SPARTAN BIOSCIENCE INC., Ottawa (CA)

(72) Inventors: Chris Harder, Dunrobin (CA); Michael Buxton, Cambridge (CA); Lawrence Dickson, Almonte (CA); John Lem, Toronto (CA); Joel Koscielski, Ottawa (CA); Derek Glennie, Richmond (CA)

(73) Assignee: Spartan Bioscience Inc., Ottawa, Ontario (CA)

(*) Notice: Subject to any disclaimer, the term of this patent is extended or adjusted under 35 U.S.C. 154(b) by 0 days.

(21) Appl. No.: 15/371,714

(22) Filed: Dec. 7, 2016

(65) Prior Publication Data

US 2017/0165670 A1     Jun. 15, 2017

Related U.S. Application Data

(60) Provisional application No. 62/266,080, filed on Dec. 11, 2015.

(51) Int. Cl.
| | |
|---|---|
| *C12P 19/34* | (2006.01) |
| *B01L 3/00* | (2006.01) |
| *G01N 35/04* | (2006.01) |

(52) U.S. Cl.
CPC ........... *B01L 3/523* (2013.01); *B01L 3/50825* (2013.01); *C12P 19/34* (2013.01); *B01L 3/50853* (2013.01);
(Continued)

(58) Field of Classification Search
CPC ....... B01L 2200/0689; B01L 2200/141; B01L 2300/042; B01L 2300/043; B01L 3/50853; C12P 19/34; G01N 2035/0405
See application file for complete search history.

(56) References Cited

U.S. PATENT DOCUMENTS

| | | |
|---|---|---|
| 2,801,017 A | 7/1957 | Cortat |
| 3,725,010 A | 4/1973 | Penhast |
| (Continued) | | |

FOREIGN PATENT DOCUMENTS

| | | |
|---|---|---|
| CA | 2256612 A1 | 12/1997 |
| CA | 2450343 A1 | 1/2003 |
| (Continued) | | |

OTHER PUBLICATIONS

Akada, R. et al., DNA Extraction Method for Screening Yeast Clones by PCR, BioTechniques, 28(4):668-674 (2000).
(Continued)

*Primary Examiner* — Betty J Forman
(74) *Attorney, Agent, or Firm* — Choate, Hall & Stewart

(57) ABSTRACT

The present disclosure provides, among other things, systems for nucleic acid amplification. Provided systems for nucleic acid amplification substantially irreversibly seal the contents of a nucleic acid amplification reaction vessel. Provided systems reduce amplification contamination, for example amplification carryover contamination. Provided systems reduce amplification of spurious nucleic acids or amplification products. The present disclosure also provides methods of amplifying nucleic acids. The present disclosure also provides methods of amplifying nucleic acids using provided systems. Provided systems and methods are useful for nucleic acid amplification.

34 Claims, 9 Drawing Sheets

(52) U.S. Cl.
CPC . *B01L 2200/0689* (2013.01); *B01L 2200/141* (2013.01); *B01L 2300/042* (2013.01); *B01L 2300/043* (2013.01); *B01L 2300/0832* (2013.01); *G01N 2035/0405* (2013.01)

(56) References Cited

U.S. PATENT DOCUMENTS

| | | | |
|---|---|---|---|
| 4,254,082 | A | 3/1981 | Schick et al. |
| 4,531,651 | A | 7/1985 | Donnelly |
| 4,581,333 | A | 4/1986 | Kourilsky et al. |
| D289,796 | S | 5/1987 | Larkin |
| 4,683,195 | A | 7/1987 | Mullis et al. |
| 4,683,202 | A | 7/1987 | Mullis |
| 4,800,159 | A | 1/1989 | Mullis et al. |
| 4,841,818 | A | 6/1989 | Plapp et al. |
| 4,889,818 | A | 12/1989 | Gelfand et al. |
| 4,965,188 | A | 10/1990 | Mullis et al. |
| 5,023,171 | A | 6/1991 | Ho et al. |
| 5,038,852 | A | 8/1991 | Johnson et al. |
| 5,066,584 | A | 11/1991 | Gyllensten et al. |
| 5,075,216 | A | 12/1991 | Innis et al. |
| 5,079,352 | A | 1/1992 | Gelfand et al. |
| 5,091,310 | A | 2/1992 | Innis |
| 5,104,792 | A | 4/1992 | Silver et al. |
| 5,118,801 | A | 6/1992 | Lizardi et al. |
| 5,176,995 | A | 1/1993 | Sninsky et al. |
| 5,187,084 | A | 2/1993 | Hallsby |
| 5,210,015 | A | 5/1993 | Gelfand et al. |
| 5,283,174 | A | 2/1994 | Arnold, Jr. et al. |
| 5,312,728 | A | 5/1994 | Lizardi et al. |
| 5,386,022 | A | 1/1995 | Sninsky et al. |
| 5,455,175 | A | 10/1995 | Wittwer et al. |
| 5,525,300 | A | 6/1996 | Danssaert et al. |
| 5,547,842 | A | 8/1996 | Hogan et al. |
| 5,552,580 | A | 9/1996 | Pfost et al. |
| 5,589,136 | A | 12/1996 | Northrup et al. |
| 5,594,123 | A | 1/1997 | Sninsky et al. |
| 5,639,604 | A | 6/1997 | Arnold, Jr. et al. |
| 5,656,207 | A | 8/1997 | Woodhead et al. |
| 5,656,439 | A | 8/1997 | Eyre |
| 5,656,493 | A | 8/1997 | Mullis et al. |
| 5,658,737 | A | 8/1997 | Nelson et al. |
| 5,731,148 | A | 3/1998 | Becker et al. |
| 5,779,981 | A | 7/1998 | Danssaert et al. |
| 5,928,907 | A | 7/1999 | Woudenberg et al. |
| 5,985,651 | A | 11/1999 | Hunicke-Smith |
| 6,033,880 | A | 3/2000 | Haff et al. |
| 6,040,166 | A | 3/2000 | Erlich et al. |
| 6,054,263 | A | 4/2000 | Danssaert et al. |
| 6,066,455 | A | 5/2000 | Kruse-Mueller et al. |
| 6,153,426 | A * | 11/2000 | Heimberg ........... B01L 3/50851 215/316 |
| 6,174,670 | B1 | 1/2001 | Wittwer et al. |
| 6,197,563 | B1 | 3/2001 | Erlich et al. |
| 6,210,958 | B1 | 4/2001 | Brust et al. |
| 6,514,736 | B1 | 2/2003 | Erlich et al. |
| 6,515,743 | B1 * | 2/2003 | Hayashi ............. G01N 21/6452 250/458.1 |
| 6,569,627 | B2 | 5/2003 | Wittwer et al. |
| 6,730,883 | B2 | 5/2004 | Brown et al. |
| 6,878,905 | B2 | 4/2005 | Brown et al. |
| 7,081,600 | B2 | 7/2006 | Brown et al. |
| 7,466,908 | B1 | 12/2008 | Lem et al. |
| 8,574,516 | B2 | 11/2013 | Teng et al. |
| 8,735,104 | B2 | 5/2014 | Harder et al. |
| 9,593,369 | B2 | 3/2017 | Jackson et al. |
| 2002/0142402 | A1 | 10/2002 | Tonoike |
| 2003/0022231 | A1 | 1/2003 | Wangh et al. |
| 2004/0115799 | A1 | 6/2004 | Gutierrez |
| 2004/0161788 | A1 * | 8/2004 | Chen ............. B01L 3/502 435/6.11 |
| 2004/0259226 | A1 | 12/2004 | Robey et al. |
| 2006/0147944 | A1 | 7/2006 | Chomczynski |
| 2006/0246493 | A1 | 11/2006 | Jensen et al. |
| 2006/0246580 | A1 * | 11/2006 | Kim ................. B01L 7/52 435/303.1 |
| 2008/0057544 | A1 | 3/2008 | Lem et al. |
| 2008/0233587 | A1 | 9/2008 | Wang et al. |
| 2008/0275229 | A1 | 11/2008 | Lem et al. |
| 2008/0311579 | A1 | 12/2008 | French et al. |
| 2010/0075296 | A1 | 3/2010 | Cloake et al. |
| 2011/0111399 | A1 | 5/2011 | O'Hara et al. |
| 2011/0212002 | A1 * | 9/2011 | Curry ................. B01L 3/5029 422/430 |
| 2013/0045477 | A1 | 2/2013 | Harder et al. |
| 2014/0335520 | A1 | 11/2014 | Jackson et al. |

FOREIGN PATENT DOCUMENTS

| | | |
|---|---|---|
| EP | 0381501 A2 | 8/1990 |
| EP | 0402995 A2 | 12/1990 |
| EP | 0640828 A1 | 3/1995 |
| EP | 0 671 473 A1 | 9/1995 |
| EP | 0747706 A1 | 12/1996 |
| WO | WO-9322058 A1 | 11/1993 |
| WO | WO-98/16313 A1 | 4/1998 |
| WO | WO-03/007677 A2 | 1/2003 |
| WO | WO-03/025226 A1 | 3/2003 |
| WO | WO-2004/029195 A2 | 4/2004 |
| WO | WO-2004/072230 A2 | 8/2004 |
| WO | WO-2004/105949 A1 | 12/2004 |
| WO | WO-2005/058501 A1 | 6/2005 |
| WO | WO-2005/100538 A1 | 10/2005 |
| WO | WO-2005/118144 A1 | 12/2005 |
| WO | WO-2008/134849 A1 | 11/2008 |
| WO | WO-2010/065924 A1 | 6/2010 |
| WO | WO-2011/121454 A2 | 10/2011 |
| WO | WO-2013/050881 A2 | 4/2013 |
| WO | WO-2017/098321 A1 | 6/2017 |

OTHER PUBLICATIONS

Aslanzadeh, J., Preventing PCR amplification carryover contamination in clinical laboratory, Ann Clin Lab Sci, 34(4):389-396 (2004).

Ausubel, F. et al., Eds., Short Protocols in Molecular Biology, Units 2.1, 2.2, 2.3, 2.4, 2.5, 3.12, and 3.13, Third Edition, John Wiley & Sons, 18 pages (1995).

Braun, D., et al., Exponential DNA Replication by Laminar Convection, Physical Review Letters, 91(15): 158103-1-158103-4 (2003).

Crews, N., et al., Continuous-flow thermal gradient PCR, Biomedical Microdevices, 10:187-195 (2007).

Dieffenback, C.W., et al., PCR Primer: A Laboratory Manual, Cold Spring Harbor Laboratory Press (1995).

European Search Report for 12838982.2, 4 pages (dated Feb. 12, 2015).

French, D.J. et al., Ultra-rapid DNA analysis using HyBeacon™ probes and direct PCR amplification from saliva, Molecular and Cellular Probes, 16(5):319-326 (2002).

Garcia-Closas, M. et al., Collection of Genomic DNA from Adults in Epidemiological Studies by Buccal Cytobrush and Mouthwash, Cancer Epidemiology, Biomarkers & Prevention, 10(6): 687-696 (2001).

Garner, H.R., et al., High-Throughput PCT, Biotechniques, 14:112-115 (1993).

Gelfand, D.H., et al., Thermostable DNA Polymerases, PCR Protocols: A Guide to Methods and Applications, San Diego, Academic Press, 129-141 (1990).

Haedicke, W., et al., Specific and Sensitive Two-Step Polymerase Chain Reaction Assay for the Detection of *Salmonella* Species, European Journal of Clinical Microbiology Infectious Diseases, 15(7): 603-607 (1996).

Hafner, G.J. et al., Isothermal Amplification and Multimerization of DNA by Bst DNA Polymerase, BioTechniques, 30:852-867 (2001).

Hendrikx, T., et al., The Impact of the Temperature Performance of Thermal (PCR) Cyclers on the Generated Results, and the Obligation for Regular Validation of PCR Thermal Cyclers, CYCLERtest BV, Landgraaf, The Netherlands (2001).

(56) References Cited

OTHER PUBLICATIONS

Higuchi, R., et al., Kinetic PCR Analysis: Real-time Monitoring of DNA Amplification Reactions, Biotechnology, 11: 1026-1030 (1993).
Higuchi, R., et al., Simultaneous Amplification and Detection of Specific DNA Sequences, Biotechnology, 10: 413-417 (1992).
Higuchi, R., Using PCR to Engineer DNA, PCR Technology: Principals and Applications for DNA Amplification, Stockton Press, 61-70 (1989).
Holland, P.M., et al., Detection of specific polymerase chain reaction product by utilizing the 5'->3' exonuclease activity of *Thermus aquatics* DNA polymerase, Proceedings of the National Academy of the USA, 88:7276-7280 (1991).
Innis, M.A. et al., PCR Protocols: A Guide to Methods and Applications, Academic Press, Inc., 8 pages (1990).
Internation Search Report for PCT/CA2008/000310, 1 page (dated May 26, 2008).
International Preliminary Report on Patentability for PCT/CA2005/000576, 36 pages (daed Sep. 13, 2005).
International Preliminary Report on Patentability for PCT/CA2008/000310, 5 pages (dated Jul. 8, 2009).
International Search Report for PCT/CA2005/000576, 4 pages (dated Jul. 21, 2005).
International Search Report for PCT/IB2011/001176, 5 pages (dated Jan. 4, 2012).
International Search Report for PCT/IB2012/002849, 2 pages (dated Apr. 10, 2013).
McPherson, M.J. et al., PCR: A Practical Approach, IRL Press (1991).
Morel, G., et al., In situ reverse transcription-polymerase chain reaction. Applications for light and electron microcopy, Biology of the Cell, 90: 137-154 (1998).
Morrison, L.E., et al., Sensitive fluorescence-based thermodynamic and kinetic measurements of DNA hybridization in solution, Biochemistry, 32: 3095-3104 (1993).
Nelson, D.L., et al., Lehninger—Principles of Biology, 4th Ed., W. H. Freeman & Company, New York, NY, 2005, only pp. 319-321 supplied.
Neumaier, M., et al., Fundamentals of quality assessment of molecular amplification methods in clinical diagnostics, Clinical Chemistry, 44(1): 12-26 (1998).
Ochert, A.S. et al., Inhibitory Effect of Salivary Fluids on PCR: Potency and Removal, Genome Research, 3:365-368 (1994).
Saiki, R.K. The Design and Optimization of the PCR, PCR Technology, pp. 7-16 (1989).
Saiki, R.K., Amplification of Genomic DNA in PCR Protocols: A Guide to Methods and Application, Academic Press, Inc., pp. 13-20 (1990).
Saiki, R.K., et al., Enzymatic Amplification of Beta-Globin Genomic Sequences and Restriction Site Analysis for Diagnosis of Sickle Cell Anemia, Science, 230(4732): 1350-1354 (1985).
Sambrook, J. et al., Molecular Cloning: A Laboratory Manual, Second Edition, Cold Spring Harbor Laboratory Press, 30 pages (1989).
Spangler, R. et al., Optimizing Taq Polymerase Concentration for Improved Signal-to-Noise in the Broad Range Detection of Low Abundance Bacteria, PLoS One, Public Library of Science, 4(9):1-9 (2009).
Supplementary European Search Report for EP 05734024.2, 3 pages (dated Mar. 15, 2010).
Tanabe, S. et al., A Real-Time Quantitative PCR Detection Method for Pork, Chicken, Beef, Mutton, and Horseflesh in Foods, Bioscience, Biotechnology, and Biochemistry, 71(12): 3131-3135 (2007).
Wang, S. and Levin, R., Thermal Factors Influencing Detection in Vibrio Vulnificus Using Real-time PCR, Journal of Microbiological Methods, 69: 358-363 (2007).
Weyant, R.S. et al., Effect of Ionic and Nonionic Detergents on the Taq Polymerase, BioTechniques, 9:308-309 (1990).
Wharam, S.D. et al., Specific detection of DNA and RNA targets using a novel isothermal nucleic acid amplification assay based on the formulation of a three-way junction structure, Nucleic Acid Research, 29 (11):e54 (2001).
Whelen, A.G. et al., Direct Genotypic Detection of *Mycobacterium tuberculosis* Rifampin Resistance in Clinical Specimens by Using Single-Tube Heminested PCR, Journal of Clinical Microbiology, 33(3):556-561 (1995).
Wittwer, C.T. and Garling, D.J., Rapid Cycle DNA Amplification: Time and Temperature Optimization, BioTechniques, 10(1): 76-83 (1991).
Wittwer, C.T., et al., Automated polymerase chain reaction in capillary tubes with hot air, Nucleic Acids Research, 17: 4353-4357 (1989).
Wittwer, C.T., et al., Rapid Cycle DNA Amplification, The Polymerase Chain Reaction, 174-181 (1994).
Written Opinion for PCT/CA2005/000576, 6 pages (dated Jul. 21, 2005).
Written Opinion for PCT/CA2008/000310, 4 pages (dated May 26, 2008).
Written Opinion for PCT/IB2011/001176, 5 pages (dated Jan. 4, 2012).
Written Opinion for PCT/IB2012/002849, 4 pages (dated Apr. 10, 2013).
International Search Report for PCT/IB2016/001840, 4 pages, dated Mar. 30, 2017.
Written Opinion for PCT/IB2016/001840, 5 pages, dated Mar. 31, 2017.

\* cited by examiner

SYSTEMS AND METHODS FOR NUCLEIC ACID AMPLIFICATION

CROSS-REFERENCE TO RELATED APPLICATION

This patent application claims the benefit of priority of U.S. patent application No. 62/266,080, filed on Dec. 11, 2015, the contents of which are hereby incorporated by reference in their entirety for all purposes herein.

BACKGROUND

Nucleic acid amplification technology is used to amplify nucleic acids or specific regions of nucleic acids. The amplification process is capable of taking extremely small amounts of a nucleic acid sample and generating copies of a particular sequence, portion or fragment thereof. Nucleic acid amplification reactions are useful as diagnostic tools in clinical laboratory settings.

SUMMARY

Among other things, the present disclosure provides systems useful for amplification of nucleic acids. The present disclosure also provides methods of using such amplification systems.

Implementations of the present disclosure are useful with a wide range of applications, including but not limited to: cloning, disease detection, disease diagnosis, forensic analysis, genetic mapping, genetic testing, nucleic acid sequencing, tissue typing, etc.

The present disclosure encompasses a recognition that nucleic acid amplification reactions are sensitive to contamination. The present disclosure encompasses a recognition that contamination from amplification of spurious nucleic acids results in false or misleading diagnostic or clinical outcomes. The present disclosure encompasses a recognition that contamination from, for example, amplicons, can occur due to nucleic acid amplification reaction containers that are accessible and/or not secure.

The present disclosure encompasses a recognition that traditional nucleic acid amplification reaction vessels are susceptible to accidentally opening and exposing an operator and/or an environment to, for example, amplicons, a nucleic acid amplification reaction mixture, and/or nucleic acid amplification reaction reagents.

In some embodiments, provided apparatus and systems provide an environment, a vessel to amplify nucleic acids.

In some embodiments, a system for substantially irreversibly sealing a nucleic acid amplification reaction vessel, includes: a base, which includes: a top surface of a base and a bottom surface of a base, and an opening in a top surface of a base defining a passage that extends from an opening in a top surface of a base to an opening in a bottom surface of a base; a nucleic acid amplification reaction vessel which is seated within a passage and protrudes through an opening in a bottom surface of a base, including: a receptacle portion distal to a bottom surface of a base for holding a nucleic acid amplification reaction mixture, walls of a nucleic acid amplification reaction vessel, including an inner surface, wherein the walls of a nucleic acid amplification reaction vessel extend from a receptacle portion of a nucleic acid amplification reaction vessel towards a bottom surface of a base, and a collection cap, including: a sample collecting tip, a top portion of a collection cap distal to a sample collecting tip of a collection cap, and an outer surface of a collection cap between a sample collecting tip of a collection cap and a top portion of a collection cap, wherein when a collection cap is inserted through a passage and into a nucleic acid amplification reaction vessel, an outer surface of a collection cap contacts an inner surface of the walls of a nucleic acid amplification reaction vessel, and when sealed, a top portion of a collection cap is recessed beneath an opening in a top surface of a base so that a collection cap is inaccessible.

In some embodiments, a nucleic acid amplification reaction vessel is removable from a bottom surface of a base. In some embodiments, a removable vessel is secured to a bottom surface of a base.

In some embodiments, a nucleic acid amplification reaction mixture held within a receptacle portion of a nucleic acid amplification reaction vessel.

In some embodiments, a base includes more than one passage, so that a system can be used to substantially irreversibly seal more than one nucleic acid amplification reaction vessel.

In some embodiments, a base includes a lid that covers a top surface of a base. In some embodiments, a lid is hingedly or slidingly connected to a base.

In some embodiments, a lid includes at least one dimple or protrusion so that when a lid covers a top surface of a base, at least one dimple or protrusion aligns with and extends into an opening in a top surface of a base. In some embodiments, at least one dimple or protrusion contacts a top portion of a collection cap recessed beneath an opening in a top surface of a base.

In some embodiments, a lid is locked to a base. In some embodiments, a lid includes locking pins that engage with a base.

In some embodiments, a receptacle portion of a nucleic acid amplification reaction vessel is optically accessible.

In some embodiments, a system includes a housing, a housing includes: a top surface of a housing and a bottom surface of a housing, wherein a top surface of a housing includes a cutout that is adapted to receive a base, so that when received, a housing surrounds at least part of a base.

In some embodiments, a nucleic acid amplification reaction vessel is removable from a bottom surface of a base, and wherein a housing engages a nucleic acid amplification reaction vessel at a bottom surface of a base. In some embodiments, when a base is received by a housing, a bottom surface of a housing secures a removable vessel to a bottom surface of a base.

In some embodiments, a bottom surface of a housing includes a cutout, so that when a base is received by a housing, a receptacle portion of a nucleic acid amplification reaction vessel is optically accessible. In some embodiments, a bottom surface of a housing includes a cutout, so that when a base is received by a housing a receptacle portion of a nucleic acid amplification reaction vessel extends beneath a bottom surface of a housing.

In some embodiments, a housing is optically transparent to interrogation wavelengths.

In some embodiments, a lid that covers a cutout on a top surface of a housing. In some embodiments, a lid is hingedly or slidingly connected to a housing or a base.

In some embodiments, a lid includes at least one dimple or protrusion aligned with an opening in a top surface of a base so that when a lid covers a top surface of a housing, at least one dimple or protrusion extends into an opening in a top surface of a base. In some embodiments, a least one dimple or protrusion extends into an opening in a top surface of a base so that it contacts a top portion of a collection cap recessed beneath an opening in a top surface of a base.

In some embodiments, a lid covers a cutout on a top surface of a housing, a lid is locked to a housing or a base. In some embodiments, a lid includes locking pins that engage with a housing or a base. In some embodiments, an edge of a top surface of a housing is raised so that when a lid covers a cutout on a top surface of a housing, a lid is sunken beneath an edge.

In some embodiments, a system includes a collection cap holder, wherein a collection cap holder includes a barrel and a shaft. In some embodiments, a top portion of a collection cap is removably connected to a barrel. In some embodiments, a barrel includes a release so that when it is actuated a barrel releases a collection cap.

In some embodiments, a storage cap that covers a nucleic acid amplification reaction vessel.

In some embodiments, a method of substantially irreversibly sealing a nucleic acid amplification reaction vessel includes steps of: providing a nucleic acid amplification reaction system; adding a nucleic acid amplification reaction mixture to a receptacle portion of a nucleic acid amplification reaction vessel; inserting a sample collecting tip of a collection cap into an opening in a top surface of a base, through a passage and into a nucleic acid amplification reaction vessel; contacting an outer surface of a collection cap with an inner surface of the walls of a nucleic acid amplification reaction vessel; and recessing a top portion of a collection cap beneath an opening in a top surface of a base, thereby sealing a nucleic acid amplification reaction in a nucleic acid amplification reaction vessel. In some embodiments, a nucleic acid sample is present on a sample collecting tip of a collection cap.

In some embodiments, a system includes a lid that covers a top surface of a base, wherein after a contacting step, a method including a step of closing a lid. In some embodiments, a lid includes at least one dimple or protrusion that contacts a top portion of a collection cap, so that a step of closing a lid includes pushing a collection cap into a vessel. In some embodiments, an edge of a top surface of a housing is raised, so that a step of closing a lid includes sinking a lid beneath an edge.

In some embodiments, a system includes a collection cap holder, wherein a collection cap holder includes a barrel and a shaft, and wherein a top portion of a collection cap is removably connected to a barrel, and wherein a barrel includes a release so that when it is actuated a barrel releases a collection cap, a method including a step of actuating a release so that a barrel releases a collection cap.

In some embodiments, a method of collecting and amplifying nucleic acids using a nucleic acid amplification reaction vessel includes steps of: obtaining a nucleic acid sample; contacting a nucleic acid sample with a nucleic acid amplification mixture in a nucleic acid amplification vessel; and performing a nucleic acid amplification reaction of a nucleic acid a nucleic acid sample.

In some embodiments, a method of collecting and amplifying nucleic acids using a nucleic acid amplification reaction vessel includes a step of obtaining a nucleic acid sample and contacting a sample collecting tip of a collection cap with a nucleic acid amplification mixture without any intervening steps.

BRIEF DESCRIPTION OF THE DRAWING

The foregoing and other objects, aspects, features, and advantages of the present disclosure will become more apparent and better understood by referring to the following description taken in conjunction with the accompanying figures in which:

FIG. 1 at panel (a) shows a nucleic acid amplification reaction vessel sealed with a collection cap. FIG. 1 at panel (b) shows a nucleic acid amplification reaction vessel sealed with a storage cap.

DEFINITIONS

Figure 1:
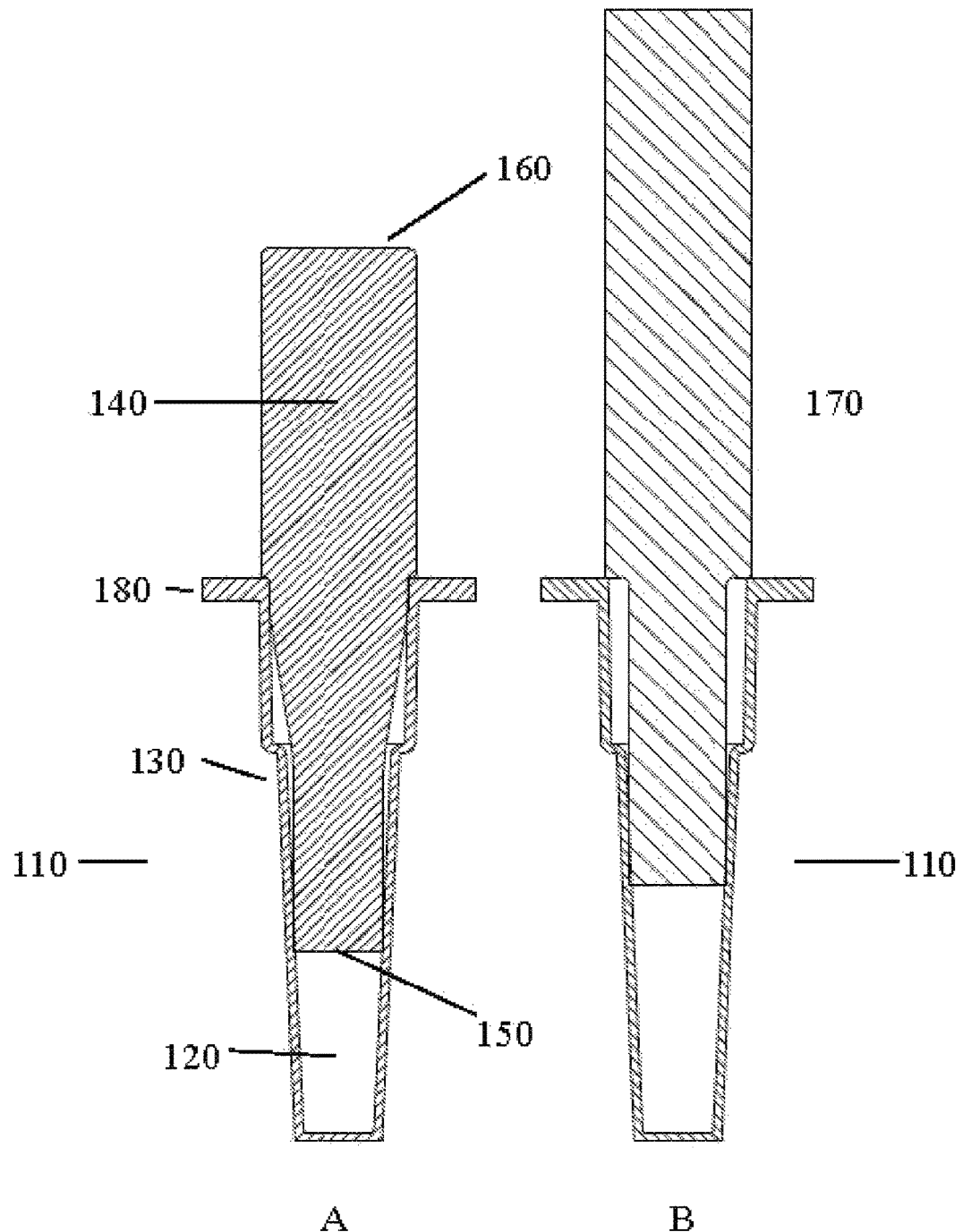
FIG. 1 shows a nucleic acid amplification reaction vessel.

In some embodiments, provided apparatus and/or methods are characterized in that they allow study of cell behavior in a variety of simulated biological environments and/or permit high-throughput analysis of cell attributes and/or responses, and/or those of agents that affect them. In order for the present disclosure to be more readily understood, certain terms are first defined below. Additional definitions for the following terms and other terms are set forth throughout the specification.

In this application, unless otherwise clear from context, the term "a" may be understood to mean "at least one." As used in this application, the term "or" may be understood to mean "and/or." As used in this application, the term "comprise" and variations of the term, such as "comprising" and "comprises," are not intended to exclude other additives, components, integers or steps.

As used in this application, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

"Amplification" or "Amplify": As used herein, the term "amplification" or "amplify" refers to methods known in the art for copying a target sequence from a template nucleic acid, thereby increasing the number of copies of the target sequence in a sample. Amplification may be exponential or linear. A template nucleic acid may be either DNA or RNA. The target sequences amplified in this manner form an "amplified region" or "amplicon." While the exemplary methods described hereinafter relate to amplification using PCR, numerous other methods are known in the art for amplification of target nucleic acid sequences (e.g., isothermal methods, rolling circle methods, etc.). The skilled artisan will understand that these other methods may be used either in place of, or together with, PCR methods. See, e.g., Saiki, "Amplification of Genomic DNA" in *PCR Protocols*, Innis et al. (1990). Eds. Academic Press, San Diego, Calif. pp 13-20; Wharam et al. (2001). *Nucleic Acids Res.* 29(11): E54-E54; Hafner et al. (2001). *Biotechniques.* 30(4): 852-6, 858, 860 passim. Further amplification methods suitable for use with the present methods include, for example, reverse transcription PCR (RT-PCR), ligase chain reaction (LCR), transcription-based amplification system (TAS), nucleic acid sequence based amplification (NASBA) reaction, self-sustained sequence replication (3 SR), strand displacement amplification (SDA) reaction, boomerang DNA amplification (BDA), Q-beta replication, or isothermal nucleic acid sequence based amplification.

"Corresponding to": As used herein, the term "corresponding to" is often used to designate a structural element or moiety in an agent of interest that shares a position (e.g., in three-dimensional space or relative to another element or moiety) with one present in an appropriate reference agent. For example, in some embodiments, the term is used to refer to position/identity of a residue in a polymer, such as an amino acid residue in a polypeptide or a nucleotide residue in a nucleic acid. Those of ordinary skill will appreciate that, for purposes of simplicity, residues in such a polymer are often designated using a canonical numbering system based on a reference related polymer, so that a residue in a first polymer "corresponding to" a residue at position 190 in the reference polymer, for example, need not actually be the $190^{th}$ residue in the first polymer but rather corresponds to the residue found at the $190^{th}$ position in the reference polymer; those of ordinary skill in the art readily appreciate how to identify "corresponding" amino acids, including through use of one or more commercially-available algorithms specifically designed for polymer sequence comparisons.

"Fragment": A "fragment" of a material or entity as described herein has a structure that includes a discrete portion of the whole, but lacks one or more moieties found in the whole. In some embodiments, a fragment consists of such a discrete portion. In some embodiments, a fragment consists of or comprises a characteristic structural element or moiety found in the whole.

"Nucleic acid": as used herein, in its broadest sense, refers to any compound and/or substance that is or can be incorporated into an oligonucleotide chain. In some embodiments, a nucleic acid is a compound and/or substance that is or can be incorporated into an oligonucleotide chain via a phosphodiester linkage. As will be clear from context, in some embodiments, "nucleic acid" refers to individual nucleic acid residues (e.g., nucleotides and/or nucleosides); in some embodiments, "nucleic acid" refers to an oligonucleotide chain comprising individual nucleic acid residues. In some embodiments, a "nucleic acid" is or comprises RNA; in some embodiments, a "nucleic acid" is or comprises DNA. In some embodiments, a nucleic acid is, comprises, or consists of one or more natural nucleic acid residues. In some embodiments, a nucleic acid is, comprises, or consists of one or more nucleic acid analogs. In some embodiments, a nucleic acid analog differs from a nucleic acid in that it does not utilize a phosphodiester backbone. For example, in some embodiments, a nucleic acid is, comprises, or consists of one or more "peptide nucleic acids", which are known in the art and have peptide bonds instead of phosphodiester bonds in the backbone, are considered within the scope of the present invention. Alternatively or additionally, in some embodiments, a nucleic acid has one or more phosphorothioate and/or 5'-N-phosphoramidite linkages rather than phosphodiester bonds. In some embodiments, a nucleic acid is, comprises, or consists of one or more natural nucleosides (e.g., adenosine, thymidine, guanosine, cytidine, uridine, deoxyadenosine, deoxythymidine, deoxy guanosine, and deoxycytidine). In some embodiments, a nucleic acid is, comprises, or consists of one or more nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, 0(6)-methylguanine, 2-thiocytidine, methylated bases, intercalated bases, and combinations thereof). In some embodiments, a nucleic acid comprises one or more modified sugars (e.g., 2'-fluororibose, ribose, 2'-deoxyribose, arabinose, and hexose) as compared with those in natural nucleic acids. In some embodiments, a nucleic acid has a nucleotide sequence that encodes a functional gene product such as an RNA or protein. In some embodiments, a nucleic acid includes one or more introns. In some embodiments, nucleic acids are prepared by one or more of isolation from a natural source, enzymatic synthesis by polymerization based on a complementary template (in vivo or in vitro), reproduction in a recombinant cell or system, and chemical synthesis. In some embodiments, a nucleic acid is at least 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 20, 225, 250, 275, 300, 325, 350, 375, 400, 425, 450, 475, 500, 600, 700, 800, 900, 1000, 1500, 2000, 2500, 3000, 3500, 4000, 4500, 5000 or more residues long. In some embodiments, a nucleic acid is single stranded; in some embodiments, a nucleic acid is double stranded. In some embodiments a nucleic acid has a nucleotide sequence comprising at least one element that encodes, or is the complement of a sequence that encodes, a polypeptide. In some embodiments, a nucleic acid has enzymatic activity.

"Sample": As used herein, the term "sample" typically refers to a biological sample obtained or derived from a source of interest, as described herein. In some embodiments, a source of interest comprises an organism, such as an animal or human. In some embodiments, a biological sample is or comprises biological tissue or fluid. In some embodiments, a biological sample may be or comprise bone marrow; blood; blood cells; ascites; tissue or fine needle biopsy samples; cell-containing body fluids; free floating nucleic acids; sputum; saliva; urine; cerebrospinal fluid, peritoneal fluid; pleural fluid; feces; lymph; gynecological fluids; skin swabs; vaginal swabs; oral swabs; nasal swabs; washings or lavages such as a ductal lavages or broncheoalveolar lavages; aspirates; scrapings; bone marrow specimens; tissue biopsy specimens; surgical specimens; feces, other body fluids, secretions, and/or excretions; and/or cells therefrom, etc. In some embodiments, a biological sample is or comprises cells obtained from an individual. In some embodiments, obtained cells are or include cells from an individual from whom the sample is obtained. In some embodiments, a sample is a "primary sample" obtained directly from a source of interest by any appropriate means. For example, in some embodiments, a primary biological sample is obtained by methods selected from the group consisting of biopsy (e.g., fine needle aspiration or tissue biopsy), surgery, collection of body fluid (e.g., blood, lymph, feces etc.), etc. In some embodiments, as will be clear from context, the term "sample" refers to a preparation that is obtained by processing (e.g., by removing one or more components of and/or by adding one or more agents to) a primary sample. For example, filtering using a semi-permeable membrane. Such a "processed sample" may comprise, for example nucleic acids or proteins extracted from a sample or obtained by subjecting a primary sample to techniques such as amplification or reverse transcription of mRNA, isolation and/or purification of certain components, etc.

"Substantially": As used herein, the term "substantially", and grammatical equivalents, refer to the qualitative condition of exhibiting total or near-total extent or degree of a characteristic or property of interest. One of ordinary skill in the art will understand that biological and chemical phenomena rarely, if ever, go to completion and/or proceed to completeness or achieve or avoid an absolute result.

DETAILED DESCRIPTION OF CERTAIN EMBODIMENTS

Among other things, the present disclosure provides systems useful for amplifying nucleic acids. Various embodiments according to the present disclosure are described in detail herein. In particular, in some embodiments, the present disclosure describes systems and methods for performing a nucleic acid amplification reaction. Implementations of the present disclosure are useful with a wide range of applications, including but not limited to: basic research, clinical medicine development, cloning, disease detection, disease diagnosis, forensic analysis, genetic mapping, genetic testing, identifying genetic mutation, industrial quality control, nucleic acid sequencing, tissue typing, etc.

Nucleic acid amplification techniques vary in complexity and procedure but operate on the same general principal. Nucleic acid amplification techniques rapidly amplify specific regions, fragments, or portions of a nucleic acid sequence.

One skilled in the art will understand that numerous methods are known in the art for amplification of nucleic acids. Indeed, varied nucleic acid amplification techniques exist, see for example, Saiki, "Amplification of Genomic DNA" in *PCR Protocols*, Innis et al., Eds. Academic Press, San Diego, Calif., 13-20 (1990); see also Wharam et al. 29 *Nucleic Acids Res.* 11, E54-E54 (2001); see also Hafner et al., 30 *Biotechniques* 4, 852-6; 858, 860 passim (2001).

In some embodiments, amplification methods suitable for the present disclosure include, for example, boomerang DNA amplification (BDA), isothermal nucleic acid sequence based amplification, helicase dependent amplification (HDA), ligase chain reaction (LCR), loop mediated isothermal amplification, multiple displacement amplification, nucleic acid sequence based amplification (NASBA) reaction, polymerase chain reaction (PCR), Q-beta replication, reverse transcription PCR (RT-PCR), rolling circle amplification (RCA), self-sustained sequence replication (3 SR), strand displacement amplification (SDA) reaction, transcription-based amplification system (TAS), or combinations thereof.

Nucleic acid amplification techniques typically include obtaining or collecting a sample of genetic material. The genetic material is contacted with nucleic acid amplification reaction mixture. The nucleic acid amplification reaction mixture involved in amplification methods, include, for example enzymes, primers, probes, buffers, etc. One skilled in the art will appreciate that these components and mixtures are readily available from commercial sources, for example, from Agilent Technologies, Bio-Rad, Biotools, Invitrogen, New England Biolabs, QIAGEN, R&D Systems, or Sigma-Aldrich, to name a few. One skilled in the art will also appreciate custom mixtures are and can be designed to address a specific or custom need.

As an example, PCR is one technique for making many copies of a specific target sequence within a template nucleic acid. PCR may be performed according to methods described in Whelan et al., 33 J. Clinical Microbiology, 3, 556-561 (1995). For example, a PCR reaction may consist of multiple amplification cycles and be initiated using a pair of primers that hybridize to the 5' and 3' ends of the target sequence. An amplification cycle may include an initial denaturation and typically up to 50 cycles of hybridization, strand elongation (or extension), and strand separation (denaturation). Hybridization and extension steps may be combined into a single step. In each cycle of a PCR reaction, a target sequence between primers is copied. Primers may hybridize to copied DNA amplicons as well as an original template DNA. A total number of copies increases exponentially with time/PCR cycle number.

Amplified target sequences or amplicons may be detected by any of a variety of well-known methods. For example, in some embodiments electrophoresis may be used (e.g., gel electrophoresis or capillary electrophoresis). Amplicons may also be subjected to differential methods of detection, for example, methods that involve the selective detection of variant sequences (e.g., detection of single nucleotide polymorphisms or SNPs using sequence specific probes). In some embodiments, amplicons are detected in real-time.

Sensitivity is a hallmark of nucleic acid amplification. Sensitivity refers to how effectively a sample is amplified. With respect to nucleic acid sequences, fragments, or portions thereof, nucleic acid techniques amplify anything and everything in a sample. This means that a nucleic acid technique can be used to find and amplify nucleic acids which may only be present in trace amounts in a sample.

The ability to amplify a tiny sample of nucleic acids can also mean that a limited sample can be compromised beyond use by contamination. That is, these amplification techniques are very vulnerable to contamination from nucleic acids present on an operator or in the environment and in particular from a prior amplified sample. Such contamination is undesirable because the spurious nucleic acids will generate false, incorrect, or inaccurate test results.

Amplicon carryover contamination, is a particularly acute problem. See for example, Aslanzadeh, *Brief Review: Preventing PCT Amplification Carryover Contamination in a Clinical Laboratory,* 34 Annals Clinical & Laboratory Science 4 (2004).

Pre-amplification and post-amplification techniques have been developed that limit amplicon carryover contamination and reduce the possibility of false, incorrect, or inaccurate results due to amplification products carryover contamination. Laboratory and clinical settings have incorporated techniques to reduce contamination. Such techniques include chemical barriers, such as cleaning with bleach; mechanical barriers, such as physical separation of laboratory areas; and/or sterilization techniques, such as ultraviolet radiation to reduce the impact of contamination.

The techniques are not fully effective and/or not effective in all circumstances, in particular, for example, point of care solutions. Generally, point of care testing is any medical test performed at or near a patient, for example, testing at the bedside, a physician's office, clinic, drug store, or in the home. Challenges to point of care testing include, for example, reliable control of testing equipment, disposable, methods, and samples. Operators in these contexts are also more likely patient care staff rather than trained operators.

In the point of care testing context, contamination has impeded or prevented mainstream implementation of nucleic acid amplification testing techniques. As noted above, even in highly controlled clinical laboratory environments contamination can create false, incorrect, or inaccurate results. Contamination in uncontrolled or less well controlled environments with less highly trained operators exacerbates contamination and its effects. Furthermore, point of care testing poses a risk of exposure to operators, medical staff, patients, and the environment from accidental exposure to genetic material, amplification products, reagents, mixtures, etc.

The present disclosure encompasses a recognition that nucleic acid amplification techniques useful for various clinical, diagnostic, treatment, etc. applications generate large numbers of amplification products. The present disclosure encompasses a recognition that when such large numbers of amplification products are intentionally or accidentally released from a nucleic acid amplification reaction vessel, the release results in contamination of the operator and the work area surrounding the contamination site. The present disclosure encompasses a recognition that contamination will result in subsequent false positive or false negative results due to amplification of foreign nucleic acids. The present disclosure encompasses a recognition that due to contamination, nucleic acid amplification techniques pose health and safety risks to animals, organisms, and/or the environment due to exposure for example to genetic material, amplification products, reagents, mixtures, etc.

Traditional apparatus, systems, and methods for nucleic acid amplification may result in contamination or are subject to contamination, including amplicon contamination. Traditional techniques, including systems and processes for reducing contamination do not prevent contamination and are not effective at containing contamination, are costly, and are labor intensive. Moreover, traditional systems and techniques do not directly transfer to point of care testing applications.

The present disclosure provides systems and methods for collecting nucleic acids, amplifying nucleic acids, and performing nucleic acid amplification testing.

Nucleic Acid Amplification Systems

In some embodiments, the present disclosure provides systems and methods for collecting and amplifying nucleic acids. In some embodiments, the present disclosure provides that once a nucleic acid amplification reaction vessel is sealed, a cap or cover that was used for sealing is not readily accessible and/or not easily removed. In some embodiments, the present disclosure provides systems and methods for collecting and amplifying nucleic acids, that substantially reduce and/or eliminate instances of accidental opening of a nucleic acid amplification reaction vessel when compared with traditional apparatus and techniques. In some embodiments, the present disclosure provides systems and methods that substantially reduce and/or eliminate instances of accidental exposure of an operator or an environment with contents of a nucleic acid amplification reaction vessel, for example, genetic material, amplification products, reagents, and/or mixtures etc. outside of a nucleic acid amplification reaction vessel when compared with traditional apparatus and techniques.

Nucleic Acid Amplification Reaction Vessel

In some embodiments, provided systems comprise a nucleic acid amplification reaction vessel. In some embodiments, a nucleic acid amplification reaction is performed in a nucleic acid amplification reaction vessel.

In some embodiments, a nucleic acid amplification reaction vessel is or comprises, for example, plastic, glass, natural polymers, synthetic polymers, metal, or combinations thereof. In some embodiments, a nucleic acid amplification reaction vessel is made of any material that does not contaminate a sample. In some embodiments, a nucleic acid amplification reaction vessel is made of any material suitable for conditions for nucleic acid amplification reactions, such as nucleic acid amplification reaction mixtures, chemical reagents and/or thermal cycling. In some embodiments, a nucleic acid amplification reaction vessel is made of polypropylene.

In some embodiments, a nucleic acid amplification reaction vessel comprises a receptacle, walls, a lip and/or an edge.

In some embodiments, a receptacle portion of a nucleic acid amplification reaction vessel is optically transparent. In some embodiments, a receptacle portion of a nucleic acid amplification reaction vessel is optically transparent to interrogation wavelengths.

In some embodiments, a receptacle portion of a nucleic acid amplification reaction vessel has a round bottom. In some embodiments, a receptacle portion of a nucleic acid amplification reaction vessel has a flat bottom. In some embodiments, a receptacle portion of a nucleic acid amplification reaction vessel is at a bottom of a nucleic acid amplification reaction vessel.

In some embodiments, a receptacle portion of a nucleic acid amplification reaction vessel is sized to contain a volume. In some embodiments, pre-amplification, a receptacle portion of a nucleic acid amplification reaction vessel contains, for example, a sample, a nucleic acid amplification reaction mixture, and/or nucleic acid amplification reaction reagents. In some embodiments, a receptacle portion of a nucleic acid amplification reaction vessel is sized to contain a range of about less than 1 nanoliter to about 1 milliliter, a range of about 1 nL to about 10 nL, a range of about 1 nL to about 1 µL, a range of about 1 µL to about 1 mL, a range of about 1 µL to about 10 µL, a range of about 1 nL to about 1.5 nL, a range of about 2 nL to about 2.5 nL, a range of about 3 nL to about 3.5 nL, a range of about 4 nL to about 4.5 nL, a range of about 5 nL to about 5.5 nL, a range of about 6 nL to about 6.5 nL, a range of about 7 nL to about 7.5 nL, a range of about 8 nL to about 8.5 nL, a range of about 9 nL to about 9.5 nL, a range of about 10 nL to about 20 nL, a range of about 30 nL to about 40 nL, a range of about 50 nL to about 60 nL, a range of about 70 nL to about 80 nL, a range of about 90 nL to about 100 nL, a range of about 200 nL to about 300 nL, a range of about 400 nL to about 500 nL, a range of about 600 nL to about 700 nL, a range of about 800 nL to about 900 nL, a range of about 1 µL to about 10 µL, a range of about 20 µL to about 30 µL, a range of about 40 µL to about 50 µL, a range of about 60 µL to about 70 µL, a range of about 80 µL to about 90 µL, a range of about 100 µL to about 200 µL, a range of about 300 µL to about 400 µL, a range of about 500 µL to about 600 µL, a range of about 700 µL to about 800 µL, a range of about 900 µL to about 1 mL or more. In some embodiments, a receptacle portion of a nucleic acid amplification reaction vessel is sized to contain a range of less than about 1 nanoliter to about 1 nL, a range of about 1.5 nL to about 2 nL, a range of about 2.5 nL to about 3 nL, a range of about 3.5 nL to about 4 nL, a range of about 4.5 nL to about 5 nL, a range of about 5.5 nL to about 6 nL, a range of about 6.5 nL to about 7 nL, a range of about 7.5 nL to about 8 nL, a range of about 8.5 nL to about 9 nL, a range of about 9.5 nL to about 10 nL, a range of about 20 nL to about 30 nL, a range of about 40 nL to about 50 nL, a range of about 60 nL to about 70 nL, a range of about 80 nL to about 90 nL, a range of about 100 nL to about 200 nL, a range of about 300 nL to about 400 nL, a range of about 500 nL to about 600 nL, a range of about 700 nL to about 800 nL, a range of about 900 nL to about 1 µL, a range of about 10 µL to about 20 µL, a range of about 30 µL to about 40 µL, a range of about 50 µL to about 60 µL, a range of about 70 µL to about 80 µL, a range of about 90 µL it to about 100 µL, a range of about 200 µL to about 300 µL, a range of about 400 µL to about 500 µL, a range of about 600 µL to about 700 µL, a range of about 800 µL to about 900 µL, a range of about 1 mL or more.

In some embodiments, a nucleic acid amplification reaction vessel has any shape, for example, rectangular, square, etc. In some embodiments, a nucleic acid amplification reaction vessel is a tube, for example an Eppendorf or Eppendorf 'style' tube.

In some embodiments, walls of a nucleic acid amplification reaction vessel extend from a receptacle portion of a nucleic acid amplification reaction vessel at a bottom of a nucleic acid amplification reaction vessel. In some embodiments, a nucleic acid amplification reaction vessel tapers outward as it extends away from a receptacle.

In some embodiments, walls of a nucleic acid amplification reaction vessel comprise an inner surface.

In some embodiments, walls of a nucleic acid amplification reaction vessel terminate at a top edge. In some embodiments, walls of a nucleic acid amplification reaction vessel terminate at a top edge defining an opening to a nucleic acid amplification reaction vessel. In some embodiments, a top edge of a nucleic acid amplification reaction vessel is about a same size and shape as its walls. In some embodiments, a top edge of a nucleic acid amplification reaction vessel has a different size or shape from its walls. In some embodiments, a top edge of a nucleic acid amplification reaction vessel comprises a lip. In some embodiments, a lip extends outward. In some embodiments, a lip extends outward providing an operator with something to grasp.

Base

In some embodiments, provided systems comprise a base.

In some embodiments, a nucleic acid amplification reaction vessel mates with a base. In some embodiments, at least one nucleic acid amplification reaction vessel mates with a base. In some embodiments, more than one nucleic acid amplification reaction vessel mates with a base. In some embodiments, multiple nucleic acid amplification reaction vessels mate with a base.

In some embodiments, a base is or comprises, for example, plastic, glass, natural polymers, synthetic polymers, metal, or combinations thereof. In some embodiments, a base is made of polypropylene.

In some embodiments, a base is optically transparent. In some embodiments, a base is optically transparent to interrogation wavelengths.

In some embodiments, a base has a shape. In some embodiments, a base is circular, rectangular, square, triangular, or any other shape. In some embodiments, a base is elongated.

In some embodiments, a base comprises a top surface and a bottom surface.

In some embodiments, a top surface of a base comprises an opening. In some embodiments, a bottom surface of a base comprises an opening. In some embodiments, an opening is similarly shaped to that of a nucleic acid amplification reaction vessel. In some embodiments, when a nucleic acid amplification reaction vessel is for example a tube or has a tubular shape, an opening on a top surface of a base has a tubular or circular shape. In some embodiments, an opening in a top surface of a base is sized to complement an outer surface of a nucleic acid amplification reaction vessel.

In some embodiments, an opening in a top surface of a base defines a passage that extends from a top surface of a base to a bottom surface of a base. In some embodiments, a passage is a through-hole. In some embodiments, a base comprises more than one opening and more than one passage through a base. In some embodiments, a base that comprises more than one opening and more than one passage through a base, those openings and/or passages are interconnected and/or overlapping. In some embodiments, a base that comprises more than one opening and more than one passage through a base, those openings and/or passages are separate from one another.

In some embodiments, when a nucleic acid amplification reaction vessel is, for example, a tube or has a tubular or circular shape, a passage has a tubular or cylindrical shape. In some embodiments, a passage is at least large enough to allow a nucleic acid amplification reaction vessel to pass through it. In some embodiments, a passage is at least large enough to allow a cap of a nucleic acid amplification reaction vessel to pass through it.

In some embodiments, a top of a nucleic acid amplification reaction vessel approximately aligns with a passage at a bottom surface of a base. In some embodiments, a top edge or a lip of a nucleic acid amplification reaction vessel aligns with a passage opening at a bottom surface of a base. In some embodiments, an opening of a nucleic acid amplification reaction vessel aligns with a passage opening at a bottom surface of a base.

In some embodiments, a nucleic acid amplification reaction vessel is attached at a bottom of a base. In some embodiments, a nucleic acid amplification reaction vessel is removably attached at a bottom of a base.

In some embodiments, a top of a nucleic acid amplification reaction vessel contacts a bottom surface of a base. In some embodiments, a top edge and/or a lip of a nucleic acid amplification reaction vessel contacts a bottom surface of a base. In some embodiments, a bottom surface of a base is configured to capture a top edge and/or lip of a nucleic acid amplification reaction vessel. In some embodiments, a nucleic acid amplification reaction vessel slidingly or hingedly connects to a bottom surface of a base. In some embodiments, a nucleic acid amplification reaction vessel secures or locks to a bottom surface of a base.

In some embodiments, a nucleic acid amplification reaction vessel is a part of a base. In some embodiments, a nucleic acid amplification reaction vessel and a base are a solid piece. In some embodiments, for example, a base is molded with a nucleic acid amplification reaction vessel when it is formed.

Collection Cap and Storage Cap

In some embodiments, provided systems comprise a collection cap.

In some embodiments, a collection cap mates with a nucleic acid amplification reaction vessel. In some embodiments, a collection cap covers a nucleic acid amplification reaction vessel. In some embodiments, a collection cap seals a nucleic acid amplification reaction vessel. In some embodiments, a collection cap seals a nucleic acid amplification reaction vessel with its contents therein. In some embodiments, a collection cap seals a nucleic acid amplification reaction mixture in a nucleic acid amplification reaction vessel. In some embodiments, a collection cap seals a nucleic acid amplification reaction mixture and a sample in a nucleic acid amplification reaction vessel.

In some embodiments, a collection cap is or comprises a natural or synthetic polymer, such as a rubber. In some embodiments, a collection cap is or comprises a natural material, such as a cotton.

In some embodiments, a collection cap is shaped about the same as that of a nucleic acid amplification reaction vessel. In some embodiments, a collection cap is shaped about the same as that of an opening of a nucleic acid amplification reaction vessel or the walls of a nucleic acid amplification reaction vessel. In some embodiments, a collection cap is shaped about the same as that of a passage of a base. In some embodiments, a collection cap is shaped about the same as that of an opening on a top surface of a base.

In some embodiments, a collection cap is sized to enter and pass through an opening in a top surface of a base. In some embodiments, a collection cap is sized to enter and pass through a passage. In some embodiments, a collection cap is sized to enter a nucleic acid amplification reaction vessel.

In some embodiments, a collection cap comprises an outer surface. In some embodiments, an outer surface of a collection cap mates with an inner surface of the walls of a nucleic acid amplification reaction vessel. In some embodiments, an outer surface of a collection cap seals with an inner surface of the walls of a nucleic acid amplification reaction vessel. In some embodiments, a seal is a compression seal. In some embodiments, a seal is a friction seal. In some embodiments, when sealed with a collection cap, contents of a nucleic acid amplification reaction are contained within a nucleic acid amplification reaction vessel.

In some embodiments, a sample is collected by contacting a source for a sample with a physical structure. In some embodiments, a collection cap is a physical structure for sample collection.

In some embodiments, a collection cap comprises a sample collection tip. In some embodiments, a sample collection tip is separate from a collection cap. In some embodiments, a sample collection tip is removably connected to a collection cap.

In some embodiments, a sample collection tip is a different material than a top portion of a collection cap. In some embodiments, a sample collection tip is a same material as a top portion of a collection cap. In some embodiments, any physical structure that collects a sample when contacted with the sample source may be used as a sample collecting tip of a collection cap. In some embodiments, a sample collecting tip of a collection cap is or comprises a swab, such as a cotton swab. In some embodiments, a sample collecting tip of a collection cap comprises an absorbent material, such as for example, cotton. In some embodiments, a sample collecting tip of a collection cap is or comprises a plastic, natural polymer, or synthetic polymer.

In some embodiments, a portion of sample collection tip of a collection cap is formed into a shape corresponding to an inner surface of the walls of a nucleic acid amplification reaction vessel.

In some embodiments, a collection cap collects a sample. In some embodiments. A sample collecting tip of a collection cap collects a sample. In some embodiments, a sample collecting tip of a collection cap collects a nucleic acid sample as a result of friction. In some embodiments, a nucleic acid sample is collected by touching and/or swiping a relevant surface.

In some embodiments, a collection cap is inserted through an opening in a base. In some embodiments, a collection cap enters and passes through a passage in a base. In some embodiments, a collection cap enters and mates with a nucleic acid amplification reaction vessel.

In some embodiments, a sample is directly introduced to a nucleic acid amplification reaction vessel.

In some embodiments, a collection cap comprises a top portion.

In some embodiments, when mated with a nucleic acid amplification reaction vessel, a top portion of a collection cap is recessed within a nucleic acid amplification reaction vessel so that it is inaccessible. In some embodiments, when mated with a nucleic acid amplification reaction vessel, a top portion of a collection cap is recessed within a passage, so that it is inaccessible. In some embodiments, when mated with a nucleic acid amplification reaction vessel, a top portion of a collection cap is recessed beneath a top surface of a base and/or beneath a top edge of a nucleic acid amplification reaction vessel, so that it is inaccessible. In some embodiments, a top portion of a collection cap is inaccessible when it cannot be grasped to remove it from a nucleic acid amplification reaction vessel.

In some embodiments, a top portion of a collection cap is grasped by a holder. In some embodiments, a top portion of a collection cap is released by a holder when a collection cap mates with a nucleic acid amplification reaction vessel. In some embodiments, a holder releases a collection cap by pushing or ejecting. In some embodiments, any structure that is capable of holding a collection cap may be used.

In some embodiments, a top portion of a collection cap comprises a hook, handle, or protrusion for grasping. In some embodiments, a holder is adapted for capture such as a hook, handle, or protrusion. In some embodiments, a holder is engineered to release a collection cap. In some embodiments, a holder can be actuated to capture and/or release a collection cap.

In some embodiments, once inserted, a hook, handle, or protrusion for grasping cannot be used to remove a collection cap from a nucleic acid amplification reaction vessel. In some embodiments, a hook, handle, or protrusion for grasping breaks away or is damaged when it is used to insert a collection cap into a nucleic acid amplification reaction vessel. In some embodiments, a hook, handle, or protrusion for grasping breaks away or is damaged with use, so that once a collection cap is sealed in a nucleic acid amplification reaction vessel, such a hook, handle, or protrusion for grasping cannot be used to remove or unseal.

In some embodiments, a system comprises a storage cap. In some embodiments, a storage cap covers a nucleic acid amplification reaction vessel. In some embodiments, a storage cap covers a nucleic acid amplification reaction vessel so that the contents do not leak out. In some embodiments, a storage cap covers a nucleic acid reaction vessel to prevent or limit contaminants from entering or falling into a nucleic acid amplification reaction vessel.

In some embodiments, a storage cap is removable from a nucleic acid amplification reaction vessel. In some embodiments, a storage cap can be reinserted into a nucleic acid amplification reaction vessel. In some embodiments, a storage cap comprises a top portion. In some embodiments, a top portion of a storage cap extends above a top edge of a nucleic acid amplification reaction vessel. In some embodiments, a top portion of a storage cap extends above a top surface of a base. In some embodiments, a top portion of a storage cap extends above a top surface of a base so that it may be grasped. In some embodiments, a top portion of a storage cap extends above a top surface of a base, so that once inserted into a nucleic acid amplification reaction vessel it may be easily removed.

In some embodiments, a storage cap includes a hook, handle, or protrusion for grasping and removing a storage cap from a nucleic acid amplification reaction vessel. In some embodiments, a storage cap comprises an outer surface. In some embodiments, when inserted into a nucleic acid amplification reaction vessel, an outer surface of a storage cap is exposed for grasping and removing a storage cap from a nucleic acid amplification reaction vessel. In some embodiments, when inserted into a nucleic acid amplification reaction vessel, an outer surface of a top portion of a storage cap is exposed for grasping and removing a storage cap from a nucleic acid amplification reaction vessel. In some embodiments, an outer surface or a hook, handle, or protrusion on a top portion of a storage cap is useful for inserting a storage cap into a nucleic acid amplification reaction vessel.

In some embodiments, when a storage cap is inserted into a nucleic acid amplification reaction vessel, a seal does not form. In some embodiments, when a storage cap is inserted into a nucleic acid amplification reaction vessel and an outer surface of a storage cap contacts an inner surface of the walls, a seal does not form. In some embodiments, when a storage cap is inserted into a nucleic acid amplification reaction vessel, a substantially irreversible seal does not form. In some embodiments, when a storage cap is inserted into a nucleic acid amplification reaction vessel and an outer surface of a storage cap contacts and inner surface of the walls, a substantially irreversible seal does not form.

In some embodiments, a top portion of a storage cap is longer than a top portion of a collection cap. In some embodiments, a top portion of a storage cap is longer that a collection cap so that it is accessible above an opening in a surface of a base. In some embodiments, when a storage cap is inserted into a nucleic acid amplification reaction vessel, a top portion of a storage cap extends above an opening in a top surface of a base.

Lid for a Base

In some embodiments, provided systems comprise a lid.

In some embodiments, a lid is or comprises, for example, plastic, glass, natural polymers, synthetic polymers, metal, or combinations thereof. In some embodiments, a base is made of polypropylene.

In some embodiments, a lid contacts at least a portion of a top surface of a base. In some embodiments, a lid covers a top surface of a base. In some embodiments, a lid is sized to cover a top surface of a base. In some embodiments, a lid is sized to cover an opening in a top surface of a base. In some embodiments, a lid covers a top surface of a base so that a recessed collection cap cannot be accessed.

In some embodiments, a lid is flat. In some embodiments, a lid comprises at least one dimple or protrusion. In some embodiments, a dimple or protrusion is aligned with an opening in a top surface of a base. In some embodiments, a dimple or protrusion is sized to fit inside an opening on a top surface of a base.

In some embodiments, a lid is hingedly connected to a base. In some embodiments, a lid is slidingly connected to a base.

In some embodiments, when a lid is closed onto a top surface of a base, a dimple or protrusion enters an opening on a top surface of a base and into a passage of a base. In some embodiments, when a lid and a dimple or protrusion enters an opening and into a passage of a base, a dimple or protrusion contacts a top portion of a collection cap. In some embodiments, when a lid is closed and a dimple or protrusion enters an opening and into a passage of a base, a dimple or protrusion contacts a top portion of a collection cap so that the collection cap cannot move. In some embodiments, when a lid is closed and a dimple or protrusion enters an opening and into a passage of a base, a dimple or protrusion contacts a top portion of a collection cap and compresses it. In some embodiments, when a lid is closed and a dimple or protrusion enters an opening and into a passage of a base, a dimple or protrusion contacts a top portion of a collection cap and compresses it and pushes a collection cap in a recess and ensures it is fully seated in a nucleic acid amplification reaction vessel.

In some embodiments, a lid is locked. In some embodiments, a lid comprises pins that engage a base. In some embodiments, a base comprises holes to receive pins protruding from a base.

In some embodiments, when a storage cap is in a nucleic acid amplification reaction vessel, a lid cannot be closed.

Housing

In some embodiments, provided systems comprise a housing.

In some embodiments, a housing is or comprises, for example, plastic, glass, natural polymers, synthetic polymers, metal, or combinations thereof. In some embodiments, a housing is made of polypropylene. In some embodiments, a housing is optically transparent.

In some embodiments, a housing is adapted to surround a base. In some embodiments, a housing is adapted to encompass a base. In some embodiments, a housing is adapted to partially surround a base. In some embodiments, a housing a shaped similar to a base.

In some embodiments, a housing comprises a top surface and a bottom surface.

In some embodiments, a top surface of a housing comprises a cutout. In some embodiments, a cutout is about the same shape as a shape of a base. In some embodiments, a cutout is about a same diameter as that of a bottom surface of a base. In some embodiments, a cutout is about a same area as that of a bottom surface of a base.

In some embodiments, a cutout is adapted to receive a base, so that when received, a housing frames and/or surrounds and/or encompasses a base. In some embodiments, a base fits within a housing.

In some embodiments, a housing engages a nucleic acid amplification reaction vessel at a bottom of a base. In some embodiments, a housing secures a nucleic acid amplification reaction vessel to a bottom of a base. In some embodiments, a bottom surface of a housing secures a receptacle portion of a nucleic acid amplification reaction vessel.

In some embodiments a bottom surface of a housing comprises a cutout. In some embodiments, a receptacle portion of a nucleic acid amplification reaction vessel passes through a cutout in a bottom surface of a housing. In some embodiments, when a receptacle portion of a nucleic acid amplification reaction vessel passes through a cutout in a bottom surface of a housing, a lip of a nucleic acid amplification reaction vessel engages a bottom surface of a housing. In some embodiments, when a receptacle portion of a nucleic acid amplification reaction vessel passes through a cutout in a bottom surface of a housing, a bottom surface of a housing secures a lip of a nucleic acid amplification reaction vessel.

In some embodiments, a receptacle portion of a nucleic acid amplification reaction vessel that is within a housing is optically accessible. In some embodiments, a bottom surface of a housing comprises a cutout. In some embodiments, a cutout exposes a receptacle portion of a nucleic acid amplification reaction vessel. In some embodiments, when a base is received by the housing comprising a cutout, a receptacle portion of a nucleic acid amplification reaction vessel extends beneath a bottom surface of a housing. In some embodiments, a housing is optically transparent to interrogation wavelengths.

Lid for a Housing

In some embodiments, a housing comprises a lid.

In some embodiments, a lid contacts a top surface of a housing. In some embodiments, a lid covers at least a portion of a top surface of a housing. In some embodiments, a lid is sized to cover a top surface of a housing. In some embodiments, a lid is sized to cover a cutout in a top surface of a housing. In some embodiments, a lid covers a cutout on a top surface of a housing. In some embodiments, a lid covers a base. In some embodiments, a lid covers a top surface of a base. In some embodiments, a lid covers a top surface of a housing so that a recessed collection cap is cannot be accessed.

In some embodiments, a lid is hingedly connected to a top surface of a housing. In some embodiments, a lid is slidingly connected to a top surface of a housing.

In some embodiments, a lid is flat. In some embodiments, a lid comprises at least one dimple or protrusion. In some embodiments, a dimple or protrusion is aligned with an opening in a top surface of a base. In some embodiments, a dimple or protrusion is sized to fit inside an opening on a top surface of a base.

In some embodiments, when a lid is closed, it covers a top surface of a housing. In some embodiments, when a lid is closed onto a top surface of a housing, a lid covers a cutout on a top surface of a housing. In some embodiments, when a lid is closed onto a top surface of a housing, a dimple or protrusion enters an opening and into a passage of a base. In some embodiments, when a lid is closed onto a top surface of a housing and a dimple or protrusion enters an opening and into a passage of a base, a dimple or protrusion contacts a top portion of a collection cap. In some embodiments, when a lid is closed onto a top surface of a housing and a dimple or protrusion enters an opening and into a passage of a base, a dimple or protrusion contacts a top portion of a collection cap so that the collection cap cannot move. In some embodiments, when a lid is closed onto a top surface of a housing and a dimple or protrusion enters an opening and into a passage of a base, a dimple or protrusion contacts a top portion of a collection cap and compresses it. In some embodiments, when a lid is closed onto a top surface of a housing and a dimple or protrusion enters an opening and into a passage of a base, a dimple or protrusion contacts a top portion of a collection cap and compresses it and pushes a collection cap in a recess and ensures it is fully seated in a nucleic acid amplification reaction vessel.

In some embodiments, a lid is locked. In some embodiments, a lid comprises pins that engage a base. In some embodiments, a lid comprises pins that engage a top surface of a housing. In some embodiments, a base comprises holes to receive pins. In some embodiments, a top surface of a housing comprises holes to receive pins.

In some embodiments, a top surface of a housing comprises a cutout. In some embodiments, when a lid covers a cutout on a top surface of a housing, a lid is sunken beneath a top surface of a housing. In some embodiments, a top surface of a housing comprises an edge. In some embodiments, an edge is raised so that when a lid covers a top surface of a housing, a lid is sunken beneath an edge. In some embodiments, when a lid is sunken beneath an edge, it is not accessible.

Systems

In some embodiments, the present disclosure also provides a system and/or kit.

In some embodiments, a system and/or kit comprises a nucleic acid amplification reaction vessel and a collection cap. In some embodiments, a system and/or kit comprises a collection cap, for example, with a sample collecting tip of a collection cap.

In some embodiments, a nucleic acid amplification reaction vessel is substantially irreversibly sealed when a collection cap is inserted into the nucleic acid amplification reaction vessel.

In some embodiments, a system and/or kit comprises a base with an opening in a top surface of the base and an opening in a bottom surface of the base and a passage there through. In some embodiments, a base is formed including a nucleic acid amplification reaction vessel. In some embodiments, a base and a nucleic acid amplification reaction vessel are separate components of a system and/or kit.

In some embodiments, a nucleic acid amplification reaction vessel is attached and/or removably attached to a base. In some embodiments, a nucleic acid amplification reaction vessel is substantially irreversibly sealed when a collection cap is inserted into an opening in a top surface of the base and into the nucleic acid amplification reaction vessel so that the top portion of the collection cap is recessed beneath a top edge of a nucleic acid amplification reaction vessel and/or a top surface of a base. In some embodiments, when recessed, a top portion of a collection cap is inaccessible.

In some embodiments, a system and/or kit comprises a base with a lid. In some embodiments, a lid is hingedly or slidingly connected to a base. In some embodiments, a lid covers a base. In some embodiments, a lid locks to a base. In some embodiments, a base including a nucleic acid amplification reaction vessel sealed with a collection cap is locked when a lid is closed. In some embodiments, a locking lid provides an additional layer of security further reducing the possibility that the nucleic acid reaction amplification reaction vessel will open. In some embodiments, a lid includes dimples or protrusions. In some embodiments, the dimples or protrusions on the lid enter the passage to fill the gap between the top portion of the collection cap and the lid. In some embodiments, dimples or protrusions provide another layer of security further reducing the possibility that the nucleic acid reaction amplification reaction vessel will open.

In some embodiments, a system and/or kit comprises a housing. In some embodiments, a housing surrounds a base. In some embodiments, a housing has a top surface and a bottom surface. In some embodiments, a housing surrounding a base has an opening in the top surface allowing access to a top surface of the base. In some embodiments, a housing surrounding a base has opening in the bottom surface allowing access for nucleic acid amplification reaction vessels to protrude below a bottom surface of the base and/or housing.

In some embodiments, a nucleic acid amplification reaction vessel is substantially irreversibly sealed when a collection cap is inserted into an opening in a top surface of a housing, into an opening in a top surface of a base and into the nucleic acid amplification reaction vessel so that the top portion of the collection cap is recessed beneath a top edge of a nucleic acid amplification reaction vessel and/or a top surface of a base and/or a top surface of a housing. In some embodiments, when recessed, a top portion of a collection cap is inaccessible.

In some embodiments, a system and/or kit comprises a housing with a lid. In some embodiments, a lid is hingedly or slidingly connected to a housing. In some embodiments, a lid covers a housing. In some embodiments, when a lid locks to a housing. In some embodiments, a housing surrounding a base including a nucleic acid amplification reaction vessel sealed with a collection cap is locked when a lid is closed. In some embodiments, a locking lid provides an additional layer of security further reducing the possibility that the nucleic acid reaction amplification reaction vessel will open. In some embodiments, a lid includes dimples or protrusions. In some embodiments, the dimples or protrusions on the lid enter the passage to fill the gap between the top portion of the collection cap and the lid. In some embodiments, dimples or protrusions provide another layer of security further reducing the possibility that the nucleic acid reaction amplification reaction vessel will open.

In some embodiments, a system and/or kit comprises a storage cap. In some embodiments, a storage cap covers a nucleic acid amplification reaction vessel. In some embodiments, when a storage cap is in a nucleic acid amplification reaction vessel, a lid to a housing cannot be closed.

In some embodiments, a system and/or kit comprises a nucleic acid amplification mixture. In some embodiments, a system and/or kit comprises a nucleic acid amplification mixture that is located within a receptacle portion of a nucleic acid amplification reaction vessel. In some embodiments, a receptacle portion of a nucleic acid amplification reaction vessel is empty. In some embodiments, a system and/or kit comprises a nucleic acid amplification mixture that is located within one or more separate containers. In some embodiments, a nucleic acid amplification reaction mixture is present in a receptacle of the nucleic acid amplification reaction vessel. In some embodiments, a nucleic acid amplification reaction mixture is stored in a separate container and added to a receptacle of the nucleic acid amplification reaction vessel.

In some embodiments, a collection cap is used by an operator to obtain a nucleic acid sample. In some embodiments, an operator swabs a location so that a sample collecting tip of the collection cap contacts a nucleic acid source.

In some embodiments, an operator grips a top portion of a collection cap to manually obtain a nucleic acid sample.

In some embodiments, when a collection cap contacts an inner surface of a nucleic acid amplification reaction vessel a sample collecting tip of a collection cap mates with a nucleic acid amplification mixture located within a receptacle portion of a nucleic acid amplification reaction vessel. In some embodiments, when a sample collecting tip of a collection cap mates with a nucleic acid amplification mixture located within a receptacle portion of a nucleic acid amplification reaction vessel, a top portion of a collection cap is inaccessible.

In some embodiments, a system and/or kit comprises a holder. In some embodiments, a holder comprises a barrel and a shaft. In some embodiments, a holder captures a collection cap. In some embodiments, a top portion of the collection cap is removably connected to the barrel. In some embodiments, a holder comprises a release. In some embodiments, when activated, an actuator releases a collection cap from a holder. In some embodiments, when released a nucleic acid sample contacts a nucleic acid amplification reaction mixture held in a receptacle. In some embodiments, when released an outer surface of the collection cap seals with an inner surface of the walls of the nucleic acid amplification reaction vessel. In some embodiments, when released top portion of the collection cap is recessed beneath a top edge of the nucleic acid amplification reaction vessel, the top surface or the base, and/or the top surface of the housing. In some embodiments, when released, the top portion of the collection cap and the contents of the nucleic acid amplification reaction vessel are inaccessible.

In some embodiments, a system and/or kit includes packaging for a nucleic acid amplification reaction vessel, a base, a collection cap, a storage cap, a housing, a lid for a base, a lid for a housing, a nucleic acid amplification reaction mixture, and/or a container for a nucleic acid amplification reaction mixture. In some embodiments, packaging wraps each component. In some embodiments, packaging sterilely wraps each component. In some embodiments, packaging connects each component to each other component. In some embodiments, packaging serially connects each component to each other component.

In some embodiments, a system and/or kit comprises a thermal cycler. In some embodiments, a system and/or kit comprises a detector, for example a fluorescence detector.

Methods

In some embodiments, the present disclosure provides methods for performing a nucleic acid amplification reaction. In some embodiments, the present disclosure provides methods for sealing a nucleic acid amplification reaction vessel. In some embodiments, the present disclosure provides methods for substantially irreversibly sealing a nucleic acid amplification reaction vessel.

In some embodiments, substantially irreversibly sealing means that a collection cap is sealed within a nucleic acid amplification reaction vessel to an extent that it is totally or near-totally irremovable. In some embodiments, substantially irreversibly sealing means that a collection cap is sealed within a nucleic acid amplification reaction vessel so that it cannot accidentally fall out of the vessel after it is sealed. In some embodiments, substantially irreversibly sealing means that a collection cap is sealed within a nucleic acid amplification reaction vessel such that an operator would need to specifically act to remove it from its nucleic acid amplification reaction vessel.

In some embodiments, provided methods comprise providing a nucleic acid amplification reaction vessel. In some embodiments, provided methods comprise providing a nucleic acid amplification reaction vessel containing a nucleic acid amplification reaction mixture. In some embodiments, provided methods comprise adding a nucleic acid amplification reaction mixture to a receptacle portion of a nucleic acid amplification reaction vessel.

In some embodiments, methods comprise mating a nucleic acid amplification reaction vessel with a base. In some embodiments, mating comprises aligning the walls of a nucleic acid amplification reaction vessel with a passage of a base.

In some embodiments, methods comprise obtaining a sample. In some embodiments, methods comprise obtaining a sample using a sample collecting tip of a collection cap.

In some embodiments, methods comprise inserting a collection cap through a passage of a base and into a nucleic acid amplification reaction vessel. In some embodiments, methods comprise contacting an outer surface of a collection cap with the walls of an inner surface of a nucleic acid amplification reaction vessel. In some embodiments, a step of contacting seals a nucleic acid amplification reaction vessel.

In some embodiments, methods comprise recessing a top portion of a collection cap beneath an opening in a top surface of a base, so that a collection cap is inaccessible. In some embodiments, methods comprise recessing a top portion of a collection cap within a passage of a base and beneath a top surface of a base, so that a collection cap is inaccessible. In some embodiments, when a top portion of a collection cap is recessed, a collection cap is inaccessible so that an operator cannot accidentally remove a collection cap from a nucleic acid amplification reaction vessel.

In some embodiments, methods comprise closing a lid. In some embodiments, closing a lid covers an opening in a top surface of a base. In some embodiments, closing a lid covers a top surface of a base. In some embodiments, closing a lid covers a cutout in a top surface of a housing. In some embodiments, when closed a dimple or protrusion present on a lid and aligned with an opening in a top surface of a base passes through the opening in a top surface of a base and into a passage contacting a top portion of a collection cap. In some embodiments, when closed a dimple or protrusion present on a lid and aligned with an opening in a top surface of a base passes through the opening in a top surface of a base and into a passage pushing on a top portion of a collection cap. In some embodiments, when closed a dimple or protrusion present on a lid and aligned with an opening in a top surface of a base passes through the opening in a top surface of a base and into a passage pushing a collection cap into a nucleic acid amplification reaction vessel.

In some embodiments, methods comprise locking a lid. In some embodiments, when locked, pins present on a lid engage holes on a top surface of a housing or a top surface of a base. In some embodiments, when pins on a lid engage a housing or base, a lid cannot be opened. In some embodiments, when a lid is closed it sinks beneath a top edge of a top surface of a housing so that it is inaccessible.

In some embodiments, a holder for holding a collection cap is used when collecting a sample.

In some embodiments, when a holder is used to insert a collection cap, methods comprise releasing a collection cap in a nucleic acid amplification reaction vessel. In some embodiments, releasing a collection cap comprises actuating a holder so that a holder releases a top portion of a collection cap.

In some embodiments, methods comprise obtaining a sample comprising nucleic acids. In some embodiments, methods comprise contacting a nucleic acid sample with a nucleic acid amplification mixture without any intervening steps. In some embodiments, methods comprise contacting a nucleic acid sample with a nucleic acid amplification mixture without purification of nucleic acids in the sample.

In some embodiments, methods comprise contacting a nucleic acid sample with a nucleic acid amplification reaction mixture in a nucleic acid amplification reaction vessel. In some embodiments, methods comprise performing a nucleic acid amplification reaction of the nucleic acid sample.

In some embodiments, a step of directly contacting without purification includes a nucleic acid sample that is not subject to a purification technique. In some embodiments, a step of directly contacting without purification includes a nucleic acid sample that is not subject to a purification technique that involves physically or chemically separating nucleic acids from other cellular components. In some embodiments, a step of directly contacting without purification means not performing any step or steps that remove a percentage by weight of the non-nucleic acid components of the original sample. In some embodiments, a percentage of the non-nucleic acid components of the sample is greater than or equal to about 1%, 2%, 3%, 4%, 5%, 6%, 7%, 8%, 9%, 10%, 15%, 20% or more prior to contacting the sample with a nucleic acid amplification reaction mixture.

In some embodiments, steps of collecting or obtaining may be achieved by, for example, placing a nucleic acid amplification mixture in a nucleic acid amplification reaction vessel, using a sample collecting tip of the collection cap to collect a sample, immediately inserting a collection cap into a nucleic acid amplification reaction vessel, so that an outer surface of the collection cap contacts with an inner surface of the walls of a nucleic acid amplification reaction vessel, so that the nucleic acid amplification reaction vessel is sealed and the nucleic acid sample contacts the nucleic acid amplification mixture.

In some embodiments, a collected sample may be subjected to an intervening step before being contacted a with nucleic acid amplification reaction mixture. In some embodiments, for example, it may be advantageous to divide a nucleic acid sample into aliquots so that more than one test may be performed for the same sample source. In some embodiments, a sample may be diluted in a container other than the nucleic acid amplification reaction vessel (e.g., by mixing a sample with a buffer) and optionally aliquoted before contacting with a nucleic acid amplification mixture in a nucleic acid amplification reaction vessel. Those skilled in the art will recognize that other similar intervening steps could be introduced into a method of the present disclosure without deviating from the scope.

EXEMPLIFICATION

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

Example 1

The present example shows a nucleic acid amplification reaction vessel in accordance with some embodiments of the present disclosure.

Referring to FIG. 1, a nucleic acid amplification reaction vessel 110 is shown in panels A and B. FIG. 1 at panel A shows a nucleic acid amplification reaction vessel 110 with a collection cap 140. FIG. 1 at panel B shows a nucleic acid amplification reaction vessel 110 with a storage cap 170. The collection cap 140 has a shorter length than the storage cap 170. A longer length of a storage cap 170 is useful to grasp and remove. In some embodiments, a shorter length of a collection cap 140 is useful so that when inserted into a nucleic acid amplification reaction vessel 110, it is not accessible and therefore cannot accidentally be removed from a nucleic acid amplification reaction vessel 110. A collection cap 140 has a top portion 160. A top portion of a collection cap 160 may be adapted so that it can be grasped and/or released by a holder (not shown). A collection cap 140 has a sample collecting tip 150. A sample collecting tip of a collection cap 150 is distal to the top portion of the collection cap 160. A nucleic acid amplification reaction vessel 110 has a receptacle portion 120. A receptacle portion of a nucleic acid amplification reaction vessel 120 is adapted to hold a nucleic acid amplification reaction mixture (not shown). A nucleic acid amplification reaction vessel 110 has walls 130. Walls of a nucleic acid amplification reaction vessel 130 extend from a receptacle portion of a nucleic acid amplification reaction vessel 120. Walls of a nucleic acid amplification reaction vessel 130 extend to lip at top edge 180. In some embodiments, a lip at top edge 180 of a nucleic acid amplification reaction vessel 110 protrudes outward in a direction that is normal with a nucleic acid amplification reaction vessel 110.

Example 2

The present example shows a nucleic acid amplification reaction vessel and specifically a seal of a nucleic acid amplification reaction vessel in accordance with some embodiments of the present disclosure.

Figure 2:
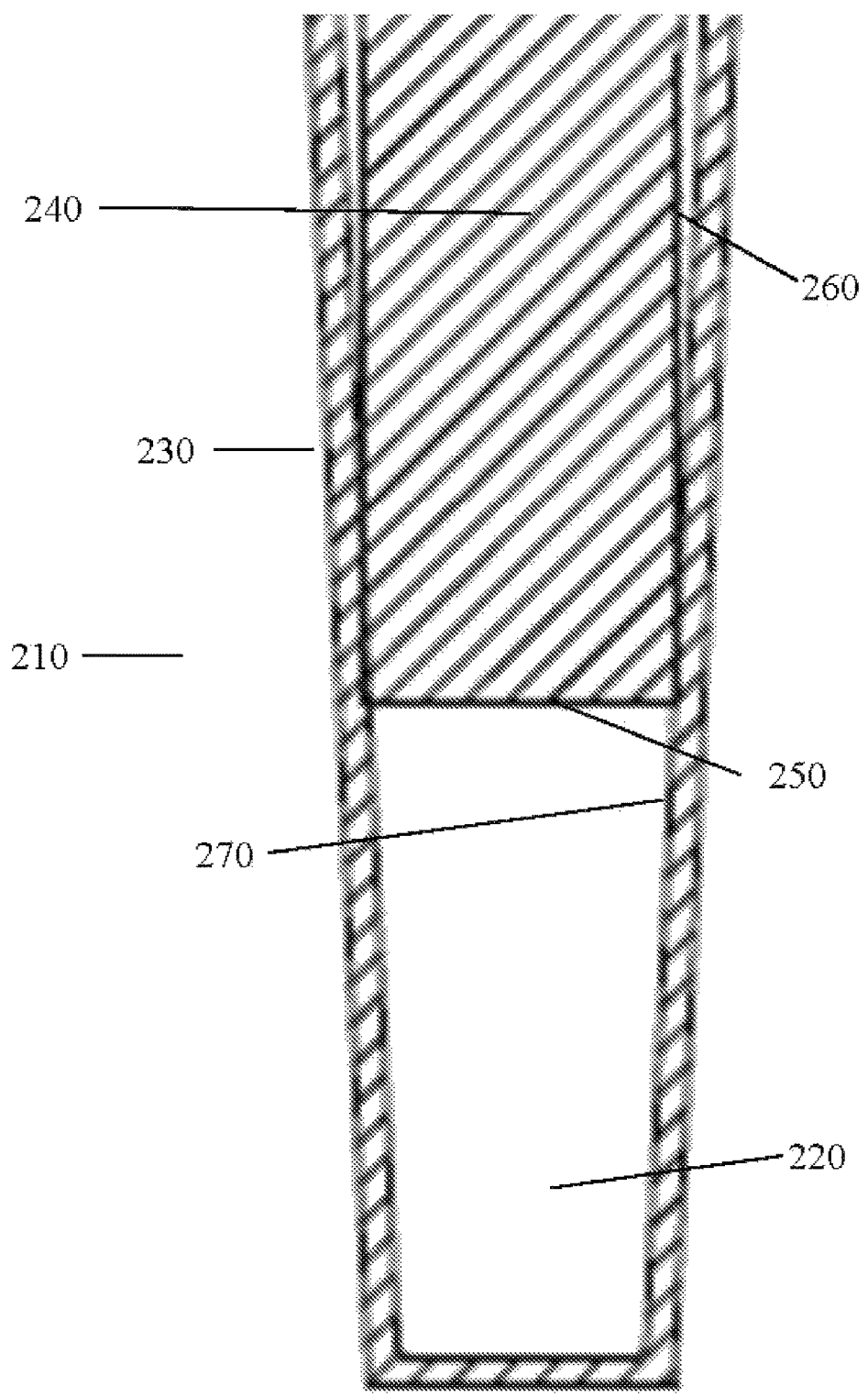
FIG. 2 shows an expanded view of a seal of a nucleic acid amplification vessel of some embodiments.

Referring to FIG. 2, a nucleic acid amplification reaction vessel 210 is shown. A nucleic acid amplification reaction vessel 210 is shown having a receptacle portion of a nucleic acid amplification reaction vessel 220 and walls 230. A collection cap 240 is shown inserted into a nucleic acid amplification reaction vessel 210. A sample collecting tip of a collection cap 250 is shown extending into a receptacle portion of a nucleic acid amplification reaction vessel 220. In some embodiments, a sample collecting tip of a collection cap 250 contacts a nucleic acid amplification reaction mixture (not shown). An outer surface 260 of a collection cap 240 contacts an inner surface 270 of the walls 230 of a nucleic acid amplification reaction vessel 210. In some embodiments, such contact forms a compression seal or a friction seal, thereby sealing a nucleic acid amplification reaction vessel 210.

Example 3

The present example shows a system for a nucleic acid amplification reaction in accordance with some embodiments of the present disclosure.

Figure 3:
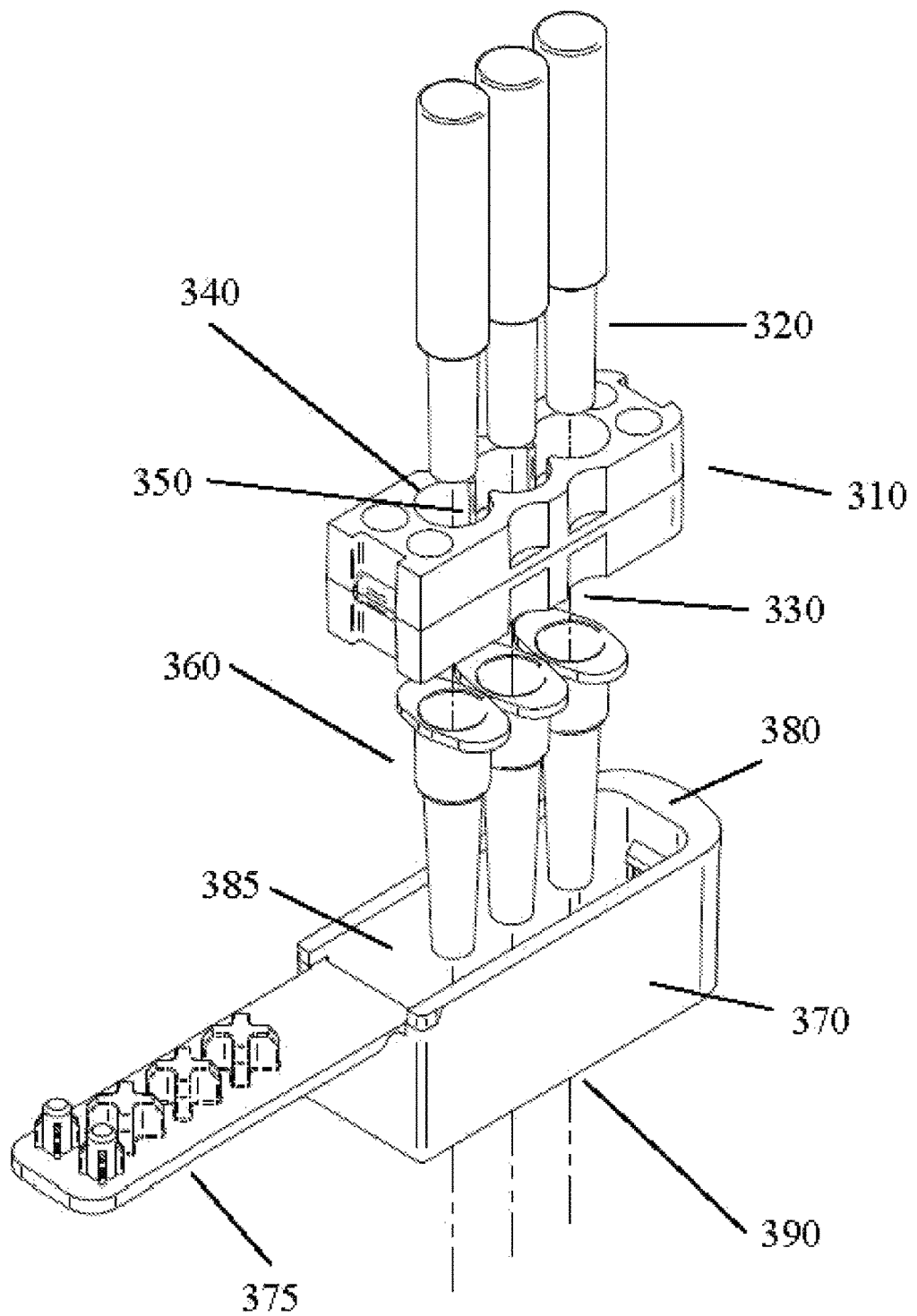
FIG. 3 shows a system for nucleic acid amplification of some embodiments.

Referring to FIG. 3, three nucleic acid amplification reaction vessels 360 are shown. A nucleic acid amplification reaction vessel 360 is shown aligned to mate with a base 310. A base 310 is shown with an opening 340 and a passage 350. Three openings 340 and passages 350 are shown. In some embodiments, openings 340 are overlapping. In some embodiments, openings 340 are separate. Three storage caps 320 are shown. A nucleic acid amplification reaction vessel 360 is shown aligned to mate with a storage cap 320. An imaginary line 330 shows alignment of a storage cap 320, a base 310, and a nucleic acid amplification reaction vessel 360. An imaginary line 330 shows alignment through an opening 340 and a passage 350. A housing 370 is shown. A cutout 385 on a top surface 380 of a housing 370 is shown. A base 310 is depicted so that it could fit inside a cutout 385 of a housing 370. A lid 375 is shown. A bottom surface of a housing 390 is shown.

Example 4

The present example shows a system for a nucleic acid amplification reaction in accordance with some embodiments of the present disclosure.

Figure 4:
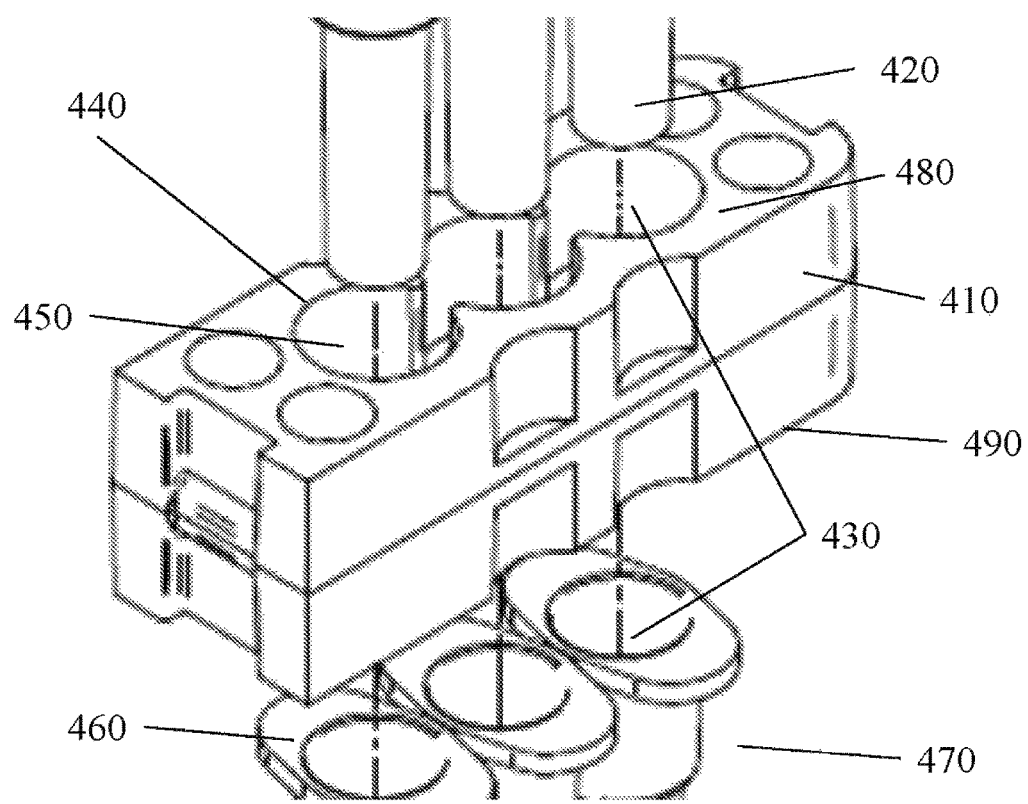
FIG. 4 shows an expanded view of a base and a plurality of openings and a plurality of passages in accordance with some embodiments.

Referring to FIG. 4, a close up of the alignment of a system for a nucleic acid amplification reaction is shown. A nucleic acid amplification reaction vessel 470 is shown. A base 410 is shown with a top surface 480 and a bottom surface 490. A lip 460 of nucleic acid amplification reaction vessel is shown aligned to mate with a bottom surface of a base 490. A top surface of a base 480 is shown with an opening 440 and a passage 450 there through. A nucleic acid amplification reaction vessel 470 is shown aligned to mate with a storage cap 420. An imaginary line 430 shows alignment of a storage cap 420, a base 410, and a nucleic acid amplification reaction vessel 470. An imaginary line 430 shows alignment through an opening 440 and a passage 450.

Example 5

The present example shows a system for a nucleic acid amplification reaction in accordance with some embodiments of the present disclosure.

Figure 5:
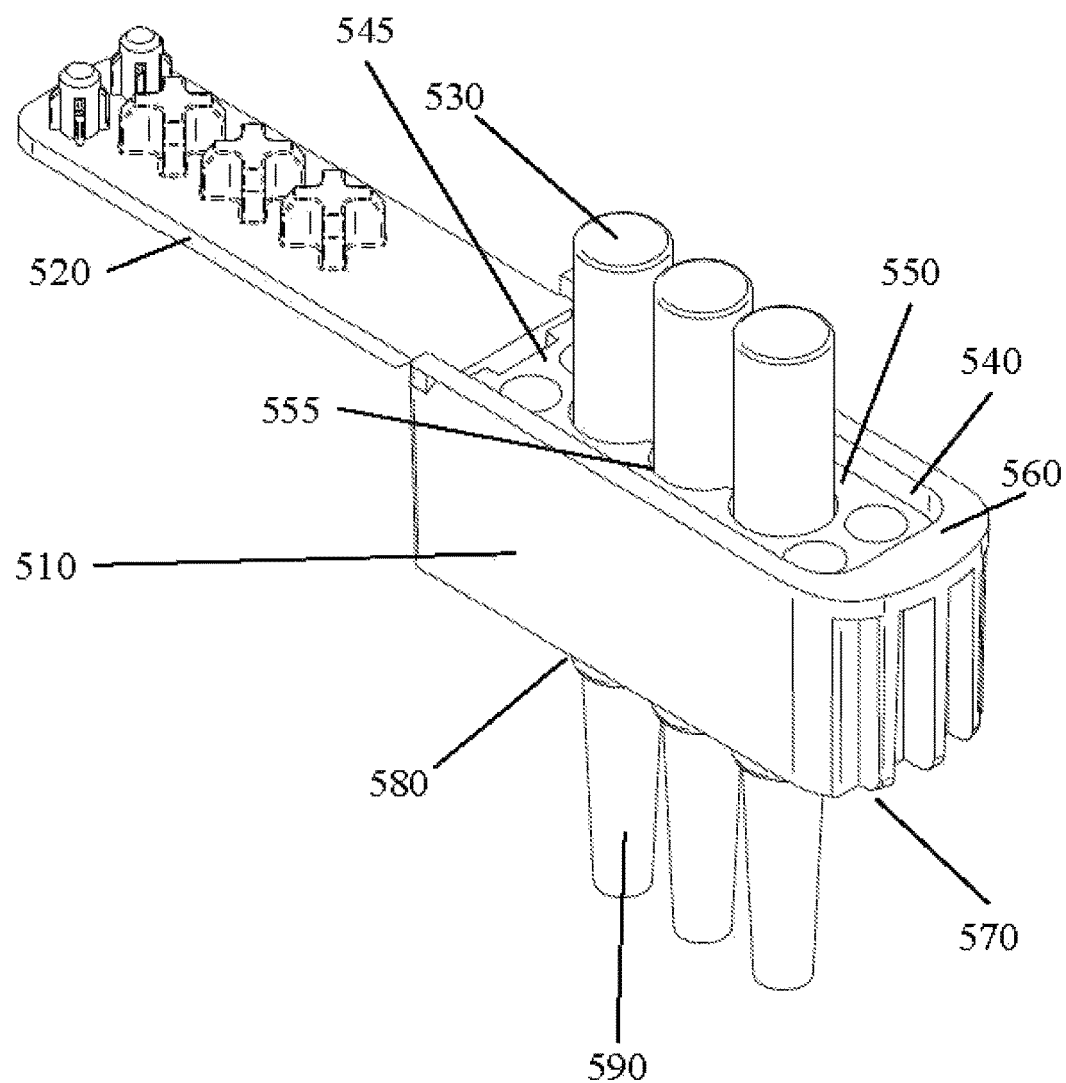
FIG. 5 shows a system for nucleic acid amplification of some embodiments.

Referring to FIG. 5, a housing 510 is shown. A top surface of a housing 560 is shown. A cutout in a top surface of a housing 540 is shown. A base 545 is shown received within a housing 510. A lid 520 is shown hingedly connected to a housing 510. Three storage caps 530 are shown inserted through a base 545 and into three nucleic acid amplification reaction vessels 590. A storage cap 530 is shown as through an opening of a base 555 in a top surface of a base 550. A nucleic acid amplification reaction vessel 590 is shown protruding out of a bottom surface of a housing 570 through a cutout 580.

Example 6

The present example shows a holder for a collection cap for a system for a nucleic acid amplification reaction in accordance with some embodiments of the present disclosure.

Figure 6:
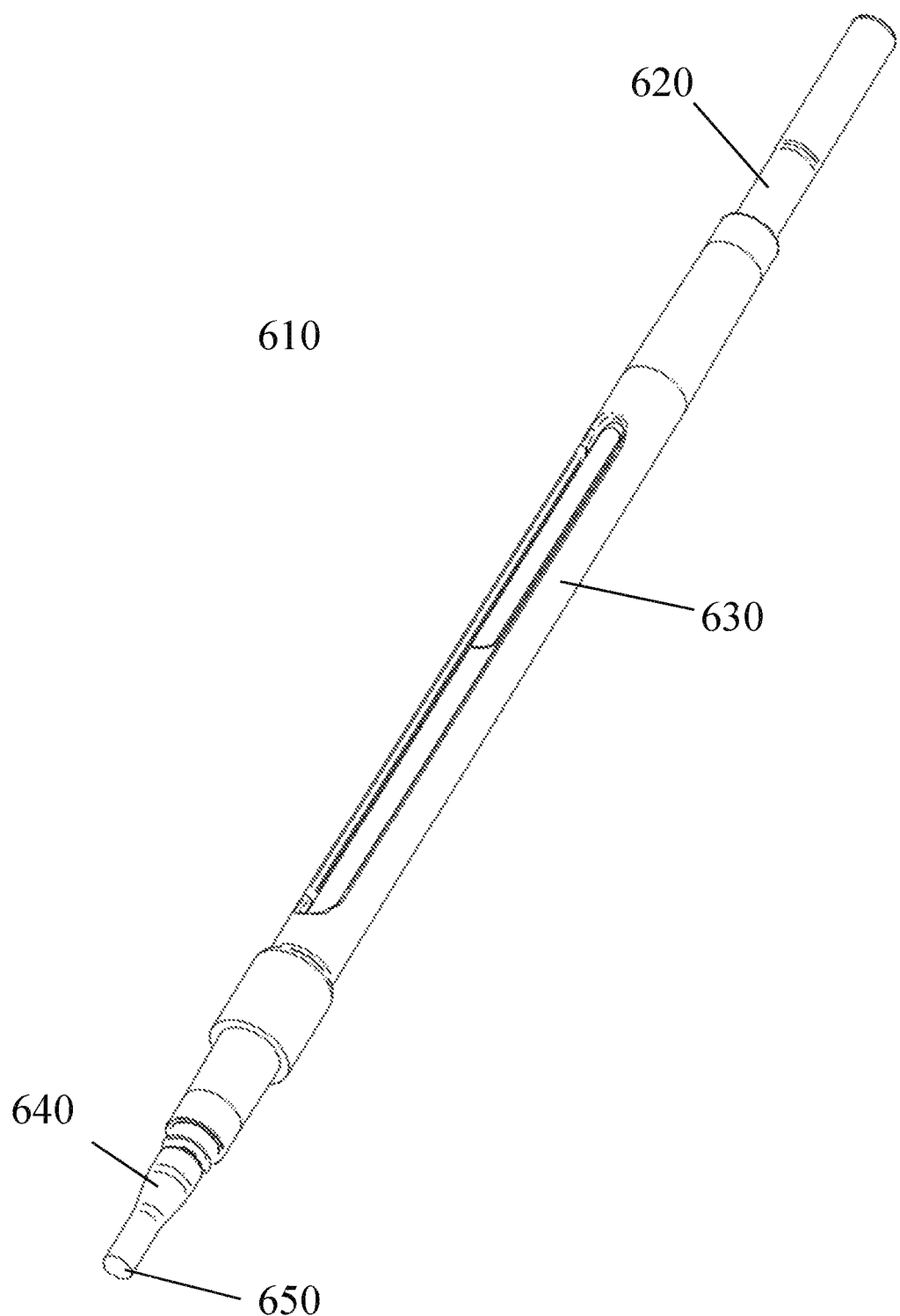
FIG. 6 shows a collection cap holder of some embodiments.

Referring to FIG. 6, a holder 610 is shown. A shaft 620 is shown at an end distal to a sample collecting tip of a collection cap 650. A barrel 630 is interposed between a shaft 620 and a collection cap 640. A shaft 620 and a barrel 630 are together adapted to create an actuator (not shown) that mechanically grasps and/or releases a collection cap 640. One of skill in the art would appreciate mechanisms for adapting a holder 610 and collection cap.

Example 7

The present example shows a holder for a collection cap with a system for a nucleic acid amplification reaction in accordance with some embodiments of the present disclosure.

Figure 7:
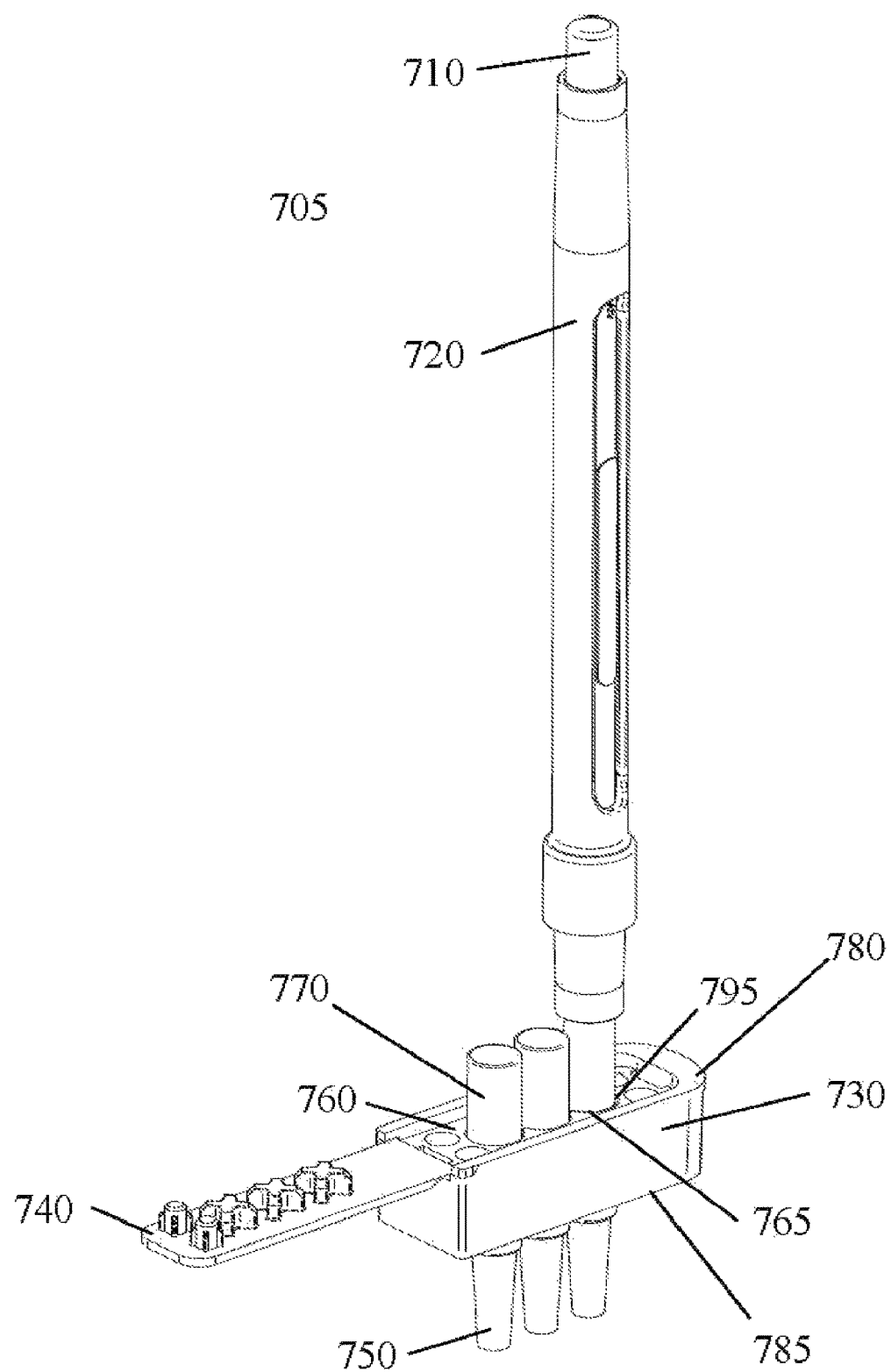
FIG. 7 shows a collection cap holder with a system for nucleic acid amplification of some embodiments.

Referring to FIG. 7, a housing 730 is shown. A lid 740 hingedly connected to a housing 730 is shown. A base 760 is shown as received by a housing 730. A holder 705 is shown. A shaft 710 and a barrel 720 are shown. A collection cap (not shown) is at an end that is distal to a shaft 710 and is being inserted through an opening 795 in a top surface of a base and into a passage 765 through a base and mated with a nucleic acid amplification reaction vessel 750. A housing 730 is shown as securing a nucleic acid amplification reaction vessel 750 to a bottom surface of a base 760. A nucleic acid amplification reaction vessel 750 extends below a bottom surface of a housing 785. Two storage caps 770 are shown as a mated with two other nucleic acid amplification reaction vessels 750. In some embodiments, storage caps 770 provide cover for the nucleic acid amplification reaction vessel and/or nucleic acid amplification reaction mixture. As shown, storage caps 770 extend upward and above a base 760 and above a top surface of a housing 780. In some embodiments, storage caps 770 are accessible, so that an operator could remove a storage cap. As shown, a storage cap 770 extends above a top surface of a housing 780, thereby preventing a lid 740 from closing.

Example 8

The present example shows a system for a nucleic acid amplification reaction in accordance with some embodiments of the present disclosure.

Figure 8:
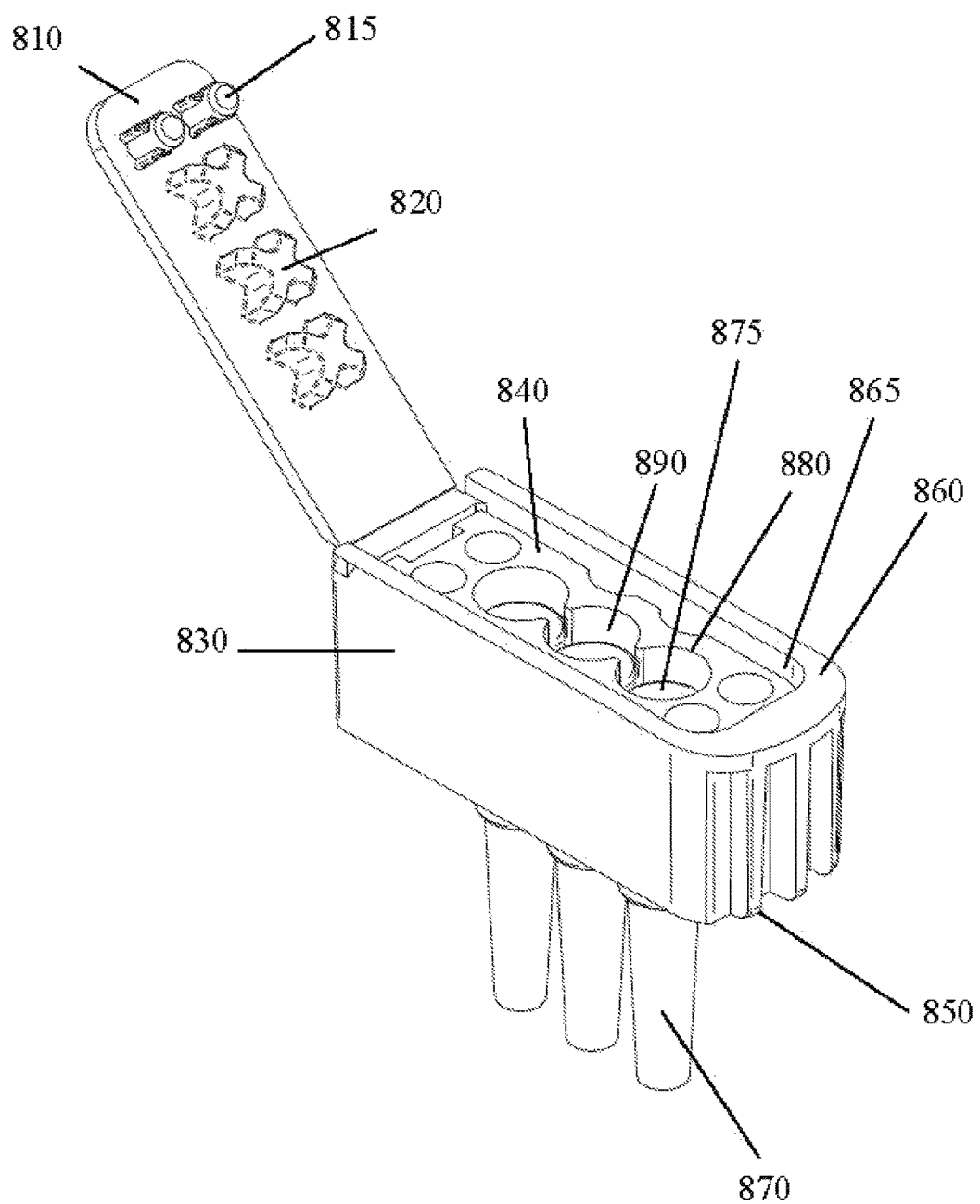
FIG. 8 shows a system for nucleic acid amplification of some embodiments.

Referring to FIG. 8, a housing 830 is shown. A lid 810 is shown hingedly connected to a housing 830. A lid 810 is shown with locking pins 815. A lid 810 is shown with dimples or protrusions 820. A housing 830 has a cutout 865 in a top surface of a housing 860. A top surface of a base 840 is shown as received by a housing 830 through a cutout 865. Three collection caps 875 are shown. A collection cap 875 is shown as inserted through an opening 880 in a top surface of a base and into a passage 890 through a base and mated with a nucleic acid amplification reaction vessel 870. A housing 830 is shown as securing a nucleic acid amplification reaction vessel 870 to a top surface of a base 840. A nucleic acid amplification reaction vessel 870 extends below a bottom surface of a housing 850. A collection cap 875, specifically a top portion of a collection cap is shown as recessed beneath an opening 880 and beneath a top surface of a base 840 and into a passage 890 of a base. In some embodiments, a top portion of collection caps 875 is recessed beneath a top surface of a base 840. In some embodiments, a top portion of collection caps 875 is recessed beneath a top surface of a housing 860, so that an operator cannot accidentally remove or loosen a collection cap. As shown, a top portion of collection caps 875 is recessed beneath a top surface of a base 840 and beneath a top surface of a housing 860, so that a lid 810 may close. In some embodiments, a dimple or protrusion 820 aligns with an opening 880 so that a dimple or protrusion 820 passes through an opening 880 to hold a top portion of a collection cap 875 in place. In some embodiments, a dimple or protrusion 820 aligns with an opening 880 so that a dimple or protrusion 820 passes through an opening 880, into a passage 890, and contacts a top portion of a collection cap 875 or compresses on a top portion of a collection cap 875 to ensure that the top portion of the collection cap 875 is sealed with its nucleic acid amplification reaction vessel 870.

Example 9

The present example shows a system for a nucleic acid amplification reaction in accordance with some embodiments of the present disclosure.

Figure 9:
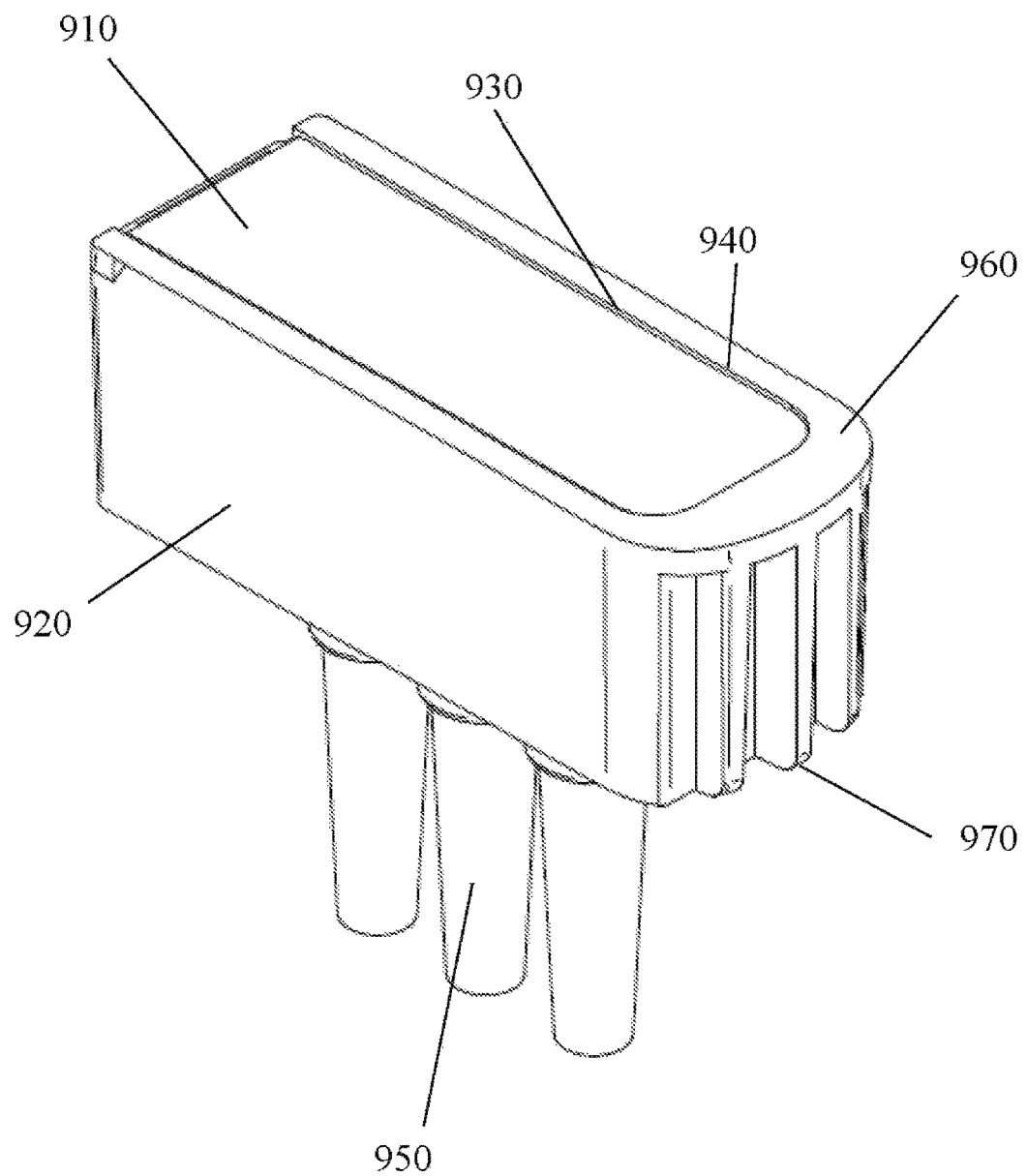
FIG. 9 shows a system for nucleic acid amplification of some embodiments.

Referring to FIG. 9, a housing 920 is shown. A lid 910 is shown connected to a housing 920. A lid 910 is shown as closed on a housing 920. A housing 920 has a top surface 960. A top surface of the housing 960 has a cutout 940. A lid 910 as shown is closed so that a lid 910 is sunken beneath a top edge 930 of a top surface of a housing 960. Three nucleic acid amplification reaction vessels 950 are shown protruding below a bottom surface of a housing 970. In some embodiments, a collection cap (not shown) is recessed beneath a top surface of a housing 960 and a base (not shown) so that the collection cap is inaccessible. In some embodiments, when a collection cap (not shown) is inaccessible, an operator cannot accidentally remove it. In some embodiments, as shown, when a collection cap (not shown) is inaccessible a lid 910 may be closed. In some embodiments, when a lid 910 is closed and sunken beneath a top surface of a housing 960, a lid 910 is inaccessible and cannot be opened.

Other Embodiments and Equivalents

While the present disclosures have been described in conjunction with various embodiments, and examples, it is not intended that they be limited to such embodiments, or examples. On the contrary, the disclosures encompass various alternatives, modifications, and equivalents, as will be appreciated by those of skill in the art. Accordingly, the descriptions, methods and diagrams of should not be read as limited to the described order of elements unless stated to that effect.

Although this disclosure has described and illustrated certain embodiments, it is to be understood that the disclosure is not restricted to those particular embodiments. Rather, the disclosure includes all embodiments, that are functional and/or equivalents of the specific embodiments, and features that have been described and illustrated. Accordingly, for example, methods and diagrams of should not be read as limited to a particular described order or arrangement of steps or elements unless explicitly stated or clearly required from context (e.g., otherwise inoperable). Moreover, the features of the particular examples and embodiments, may be used in any combination. The present disclosure therefore includes variations from the various examples and embodiments, described herein, as will be apparent to one of skill in the art.

What is claimed is:
1. A system for substantially irreversibly sealing a nucleic acid amplification reaction vessel, comprising:
  a base, comprising:
    a top surface of the base and a bottom surface of the base, and
    an opening in the top surface of the base defining a passage that extends from the opening in the top surface of the base to an opening in the bottom surface of the base;
  a nucleic acid amplification reaction vessel which is seated within the passage and protrudes through the opening in the bottom surface of the base, comprising:
    a receptacle portion distal to the bottom surface of the base for holding a nucleic acid amplification reaction mixture,
    walls of the nucleic acid amplification reaction vessel, comprising an inner surface,
      wherein the walls of the nucleic acid amplification reaction vessel extend from the receptacle portion of the nucleic acid amplification reaction vessel towards the bottom surface of the base,
  a collection cap, comprising:
    a sample collecting tip,
    a top portion of the collection cap proximal to the sample collecting tip of the collection cap, and
    an outer surface of the collection cap between the sample collecting tip of the collection cap and the top portion of the collection cap,
      wherein when the collection cap is inserted through the passage and into the nucleic acid amplification reaction vessel, the outer surface of the collection cap contacts the inner surface of the walls of the nucleic acid amplification reaction vessel thereby creating a seal, wherein a hook, handle, or protrusion for grasping cannot be used to remove the collection cap from the nucleic acid amplification reaction vessel, thereby rendering the seal irreversible, and wherein when sealed, the top portion of the collection cap is recessed beneath the opening in the top surface of the base so that the collection cap is inaccessible; and a lid comprising at least one dimple or protrusion, wherein the lid is moveable from a first position to a second position, so that when the lid is in the second position, (a) the lid covers the top surface of the base, (b) the at least one dimple or protrusion aligns with and extends into the opening in the top surface of the base, and (c) the lid is irreversibly locked to the base.

2. The system of claim 1, wherein the nucleic acid amplification reaction vessel is removable from the bottom surface of the base.

3. The system of claim 1, wherein the nucleic acid amplification reaction vessel is secured to the bottom surface of the base.

4. The system of claim 1, further comprising a nucleic acid amplification reaction mixture held within the receptacle portion of the nucleic acid amplification reaction vessel.

5. The system of claim 1, wherein the base comprises more than one passage, so that the system can be used to substantially irreversibly seal more than one nucleic acid amplification reaction vessel.

6. The system claim 1, wherein the lid is hingedly or slidingly connected to the base.

7. The system of claim 1, wherein the at least one dimple or protrusion contacts the top portion of the collection cap recessed beneath the opening in the top surface of the base.

8. The system of claim 1, wherein the lid further comprises locking pins that engage with the base.

9. The system of claim 1, wherein the receptacle portion of the nucleic acid amplification reaction vessel is optically accessible.

10. The system of claim 1, further comprising a housing, the housing comprising:

a top surface of the housing and a bottom surface of the housing, and wherein the top surface of the housing comprises a cutout that is adapted to receive the base, so that when received, the housing surrounds at least part of the base.

11. The system of claim 10, wherein the nucleic acid amplification reaction vessel is removable from the bottom surface of the base, and wherein the housing engages the nucleic acid amplification reaction vessel at the bottom surface of the base.

12. The system of claim 10, wherein when the base is received by the housing, the bottom surface of the housing secures the removable vessel to the bottom surface of the base.

13. The system of claim 10, wherein the bottom surface of the housing comprises a cutout, so that when the base is received by the housing, the receptacle portion of the nucleic acid amplification reaction vessel is optically accessible.

14. The system of claim 10, wherein the bottom surface of the housing comprises a cutout, so that when the base is received by the housing the receptacle portion of the nucleic acid amplification reaction vessel extends beneath the bottom surface of the housing.

15. The system of claim 10, wherein the housing is optically transparent to interrogation wavelengths.

16. The system of claim 10, wherein the lid covers the cutout on the top surface of the housing.

17. The system of claim 16, wherein the lid is hingedly or slidingly connected to the housing.

18. The system of claim 16, wherein the lid further comprises at least one dimple or protrusion aligned with the opening in the top surface of the base so that when the lid covers the top surface of the housing the at least one dimple or protrusion extends into the opening in the top surface of the base.

19. The system of claim 18, wherein the at least one dimple or protrusion extends into the opening in the top surface of the base so that it contacts the top portion of the collection cap recessed beneath the opening in the top surface of the base.

20. The system of claim 16, wherein when the lid covers the cutout on the top surface of the housing, the lid is locked to the housing or the base.

21. The system of claim 16, wherein the lid further comprises locking pins that engage with the housing or the base.

22. The system of claim 16, wherein an edge of the top surface of the housing is raised so that when the lid covers the cutout on the top surface of the housing, the lid is sunken beneath the edge.

23. The system of claim 1, further comprising a collection cap holder, wherein the collection cap holder comprises a barrel and a shaft.

24. The system of claim 23, wherein the top portion of the collection cap is removably connected to the barrel.

25. The system of claim 24, wherein the barrel comprises a release so that when it is actuated the barrel releases the collection cap.

26. The system of claim 1, further comprising a storage cap configured to cover the nucleic acid amplification reaction vessel when the collection cap is not inserted into the nucleic acid amplification reaction vessel.

27. A method of substantially irreversibly sealing a nucleic acid amplification reaction vessel, the method comprising steps of:

providing the system of claim 1;

adding a nucleic acid amplification reaction mixture to the receptacle portion of the nucleic acid amplification reaction vessel;

inserting the sample collecting tip of the collection cap into the opening in the top surface of the base, through the passage and into the nucleic acid amplification reaction vessel;

contacting the outer surface of the collection cap with the inner surface of the walls of the nucleic acid amplification reaction vessel; and recessing the top portion of the collection cap beneath the opening in the top surface of the base, thereby sealing the nucleic acid amplification reaction in the vessel.

28. The method of claim 27, wherein in the inserting step, a nucleic acid sample is present on the sample collecting tip of the collection cap.

29. The method of claim 27, wherein in the providing step, the system further comprises a lid that covers the top surface of the base, wherein after the contacting step, the method further comprising a step of closing the lid.

30. The method of claim 29, wherein in the providing step, the lid further comprises at least one dimple or protrusion that contacts the top portion of the collection cap, so that the step of closing the lid comprises pushing the collection cap into the vessel.

31. The method of claim 27, wherein in the providing step, the edge of the top surface of the housing is raised, so that the step of closing the lid comprises sinking the lid beneath the edge.

32. The method of claim 27, wherein in the providing step, the system further comprises a collection cap holder, wherein the collection cap holder comprises a barrel and a shaft, and wherein the top portion of the collection cap is removably connected to the barrel, and wherein the barrel comprises a release so that when it is actuated the barrel releases the collection cap, the method further comprising a step of actuating the release so that the barrel releases the collection cap.

33. A method of collecting and amplifying nucleic acids using the system of claim the method comprising steps of;
   obtaining a nucleic acid sample;
   contacting the nucleic acid sample with a nucleic acid amplification mixture in the nucleic acid amplification reaction vessel;
   and performing a nucleic acid amplification reaction of the nucleic acid sample.

34. The method of claim 33, wherein the obtaining step comprises contacting the nucleic acid sample with the sample collecting tip of the collection cap, and the contacting step comprises contacting the sample collecting tip of the collection cap with the nucleic acid amplification mixture without any intervening steps.

* * * * *

UNITED STATES PATENT AND TRADEMARK OFFICE
CERTIFICATE OF CORRECTION

PATENT NO. : 10,391,498 B2
APPLICATION NO. : 15/371714
DATED : August 27, 2019
INVENTOR(S) : Chris Harder et al.

Page 1 of 1

It is certified that error appears in the above-identified patent and that said Letters Patent is hereby corrected as shown below:

In the Claims

In Claim 29, Column 28, Line 62, please delete ""comprising"" and insert --"comprises"--.

In Claim 33, Column 29, Line 15, please insert --1,-- between "system of claim" and "the method".

Signed and Sealed this
Fourteenth Day of April, 2020

Andrei Iancu
*Director of the United States Patent and Trademark Office*